US008597931B2

(12) United States Patent
Nicaud et al.

(10) Patent No.: US 8,597,931 B2
(45) Date of Patent: Dec. 3, 2013

(54) MUTANT YEAST STRAINS CAPABLE OF ACCUMULATING A LARGE QUANTITY OF LIPIDS

(75) Inventors: Jean-Marc Nicaud, Trappes (FR); Thierry Chardot, Buc (FR); Athanasios Beopoulos, Paris (FR)

(73) Assignees: Institut National de la Recherche Agronomique (INRA), Paris (FR); Centre National de la Recherche Scientifique (CNRS), Paris (FR)

( * ) Notice: Subject to any disclaimer, the term of this patent is extended or adjusted under 35 U.S.C. 154(b) by 91 days.

(21) Appl. No.: 13/003,757

(22) PCT Filed: Jul. 8, 2009

(86) PCT No.: PCT/FR2009/000848
§ 371 (c)(1),
(2), (4) Date: Apr. 4, 2011

(87) PCT Pub. No.: WO2010/004141
PCT Pub. Date: Jan. 14, 2010

(65) Prior Publication Data
US 2011/0183387 A1    Jul. 28, 2011

(30) Foreign Application Priority Data

Jul. 11, 2008  (FR) ..................... 08 54786

(51) Int. Cl.
*C12N 1/20* (2006.01)
*C12P 7/64* (2006.01)

(52) U.S. Cl.
USPC ....................... 435/252.2; 435/134

(58) Field of Classification Search
None
See application file for complete search history.

(56) References Cited

U.S. PATENT DOCUMENTS

| | | | |
|---|---|---|---|
| 4,880,741 A | 11/1989 | Davidow et al. |
| 4,937,189 A | 6/1990 | Davidow et al. |
| 4,959,317 A | 9/1990 | Sauer |
| 5,071,764 A | 12/1991 | Davidow et al. |
| 5,254,466 A | 10/1993 | Picataggio et al. |
| 5,876,988 A | 3/1999 | Selten et al. |
| 5,965,444 A | 10/1999 | Ashikari et al. |
| 6,051,431 A | 4/2000 | Selten et al. |
| 6,063,614 A | 5/2000 | Selten et al. |
| 6,083,717 A | 7/2000 | Madzak et al. |
| 6,265,185 B1 | 7/2001 | Muller et al. |
| 6,534,315 B1 | 3/2003 | Bauer et al. |
| 6,582,951 B1 | 6/2003 | Nicaud et al. |
| 6,673,613 B2 | 1/2004 | Craft |
| 6,955,909 B1 | 10/2005 | Selten et al. |
| 2004/0014198 A1 | 1/2004 | Craft |
| 2004/0101753 A1 | 5/2004 | Hwang |
| 2004/0253621 A1 | 12/2004 | Picataggio et al. |
| 2005/0014270 A1 | 1/2005 | Picataggio et al. |
| 2005/0130280 A1 | 6/2005 | Pollak et al. |
| 2006/0019297 A1 | 1/2006 | Picataggio et al. |
| 2006/0057690 A1 | 3/2006 | Xue et al. |
| 2006/0094102 A1 | 5/2006 | Xue et al. |
| 2006/0094192 A1 | 5/2006 | Yang et al. |
| 2006/0270010 A1 | 11/2006 | Picataggio et al. |
| 2007/0004016 A1 | 1/2007 | Picataggio et al. |
| 2008/0154027 A1 | 6/2008 | Picataggio et al. |
| 2010/0041115 A1 | 2/2010 | Nicaud et al. |
| 2010/0167361 A1 | 7/2010 | Craft |
| 2011/0053219 A1 | 3/2011 | Nicaud et al. |
| 2011/0183387 A1 | 7/2011 | Nicaud et al. |
| 2012/0226059 A1 | 9/2012 | Faure et al. |
| 2013/0149754 A1 | 6/2013 | Dulermo et al. |

FOREIGN PATENT DOCUMENTS

| | | |
|---|---|---|
| WO | WO 00/12729 | 3/2000 |
| WO | WO 01/83773 | 11/2001 |
| WO | WO2005/047480 | 5/2005 |
| WO | WO2005047485 | 5/2005 |
| WO | WO 2005/118814 | 12/2005 |
| WO | WO2005/118814 | 12/2005 |
| WO | WO2006/012325 | 2/2006 |
| WO | WO2006/012326 | 2/2006 |
| WO | WO 2006/064131 | 6/2006 |
| WO | WO 2009/098263 | 8/2009 |
| WO | WO2011/064393 | 6/2011 |
| WO | WO2012/001144 | 1/2012 |

OTHER PUBLICATIONS

Yurkov et al., "Species Accumulation Curves and Incidence-Based Species Richness Estimators to Appraise the Diversity of Cultivable Yeasts from Beech Forest Soils", PLoS ONE, 2011, vol. 6, No. 8, e23671, pp. 1-9.*
Overkamp et al., "Metabolic Engineering of Glycerol Production in *Saccharomyces cerevisiae*", Appl. Environ. Microbiol. 2002, 68(6):2814.*
Kalscheuer et al., "Synthesis of Novel Lipids in Synthesis of Novel Lipids in Expression of an Unspecific Bacterial Acyltransferase", Appl. Environ. Microbiol. 2004, 70(12):7119-7125.*
Rønnow et al., "GUT2, a Gene for Dehydrogenase of Mitochondrial Saccharomy ces Glycerol 3-Phosphate cerevisiae", YEAST vol. 9 1121-1130 (1993).*

(Continued)

*Primary Examiner* — Suzanne M Noakes
(74) *Attorney, Agent, or Firm* — Lathrop & Gage LLP

(57) ABSTRACT

The subject of the present invention is a novel mutant yeast strain, particularly a *Yarrowia lipolytica* strain, capable of accumulate a large quantity of lipids. The said strain does not express the GUT2 gene. According to one variant, the invention relates to mutant yeast strains, particularly *Yarrowia lipolytica* strains, which do not express the GUT2 gene and which furthermore do not carry out the β-oxidation of lipids. Preferably, the mutant strains which do not express the GUT2 gene and which furthermore do not carry out β-oxidation of lipids do not express the POX 2 through POX 5 genes, most preferably the POX 1 through 6 genes. The subject of the invention is also a method for producing the strains according to the invention and the use of the said strains in the production of lipids.

23 Claims, 7 Drawing Sheets

(56) References Cited

OTHER PUBLICATIONS

Barth et al. (1996) "*Yarrowia lipolytica*," In: *Non conventional yeasts in biotechnology* (Wolf, K., Ed.). Springer-Verlag, Berlin, p. 313-388.
Beopoulos et al. (Dec. 2008) "Control of Lipid Accumulation in the Yeast *Yarrowia lipolytica*," *Appl. Environ. Microbiol.* 74(24):7779-7789.
Bordes et al. (Aug. 2007) "A New Recombinant Protein Expression System for High-Throughput Screening in the Yeast *Yarrowia lipolytica*." *J. Microbiological Methods* 70(3):493-502.
Fickers et al. (Dec. 2003) "New Disruption Cassettes for Rapid Gene Disruption and Marker Rescue in the Yeast *Yarrowia lipolytica*." *J. Microbiological Methods* 55(3):727-737.
Juretzek et al. (Jan. 2001) "Vectors for Gene Expression and Amplification in the Yeast *Yarrowia lipolytica*." *Yeast* 18(2):97-113.
Madzak et al. (Web Release Nov. 20, 2004) "Heterologous Production of Laccase from the Basuduintcete *Pycnoporus cinnabarinus* in the Dimorphic Yeast *Yarrowia lipolytica*," *FEMS Yeast Research* 5:635-646.
Maftahi et al. (1996) "Sticky-End Polymerase Chain Reaction Method for Systematic Gene Disruption in *Saccharomyces cerevisiae*," *Yeast* 12:859-868.
Mauersberger et al. (Sep. 2001) "Insertional Mutagenesis in the n-Alkane-Assimilating Yeast *Yarrowia lipolytica* : Generation of Tagged Mutations in Genes Involved in Hydrophobic Substrate Utilization," *J. Bacteriol.* 183(17):5102-5109.
Mlickova et al. (Jul. 2004) "Lipid Accumulation, Lipid Body Formation, and Acyl Coenzyme A Oxidase of the Yeast *Yarrowia lipolytica*," *Appl. Environ. Microbiol.* 70(7):3981-3924.
Mlickova et al. (May 4, 2004) "Acyl-CoA Oxidase, A Key Step for Lipid Accumulation in the Yeast *Yarrowia lipolytica*," *J. Mol. Catal. B* 28(2-3):81-85.
Sauer, B. (Jun. 1987) "Functional Expression of the Cre-Lox Site-Specific Recombination System in the Yeast *Saccharomyces cervisiae*," *Mol. Cell. Biol.* 7(6):2087-2096.

Thevenieau et al. (May 6, 2007) "Characterization of 1-2 *Yarrowia lipolytica* Mutants Affected ub Hydrophobic Substrate Utilization," *Fungal Genet. Biol.* 44(6):531-542.
Wang et al. (Sep. 1999) "Evaluation of Acyl CoA oxidase (Aox) Isozymes Function in the n-Alkanes-Assimilating Yeast *Yarrowia lipolytica*," *J. Bacteriol.* 181(17):5140-5148.
Wache, Y. et al. (Dec. 2001) "Role of beta-oxidation enzymes in gamma-decalactone production by the yeast *Yarrowia lipolytica*," Applied Environ. Microbiol.67(12):5700-5704.
Beopoulos A. et al. (Feb. 2012) Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts, Appl. Microbiol. Biotechnol. 93:1523-1537.
Bepoulos A. et al. (May 2011) "An overview of lipid metabolism in yeast and its impact on biotechnological processes," Appl. Microbiol. Biotechnol. 90(4):1193-1206.
Beopoulos et al. (Nov. 2009) "*Yarrowia lipolytica* as a model for bio-oil production," Prog. Lipid Res. 48:375-387.
Kurat et al. (Jun. 2005) "Obese Yeast: Triglyceride Lipolysis is Functionally Conserved from Mammals to Yeast," J. Biol. Chem. 281(1) 491-500.
Madzak et al. (Apr. 2004) "Heterologous Protein Expression and Secretion in the Non-Conventional Yeast *Yarrowia lipolytica*: A Review," J. Biotechnology 109(91-92):63-81.
Wache, Y. et al. (Dec. 2001) "Role of beta-oxidation enzymes in gamma-decalactone production by the yeast *Yarrowia lipolytica*," Applied Environ. Microbiol. 67(12):5700-5704.
International Search Report (English) issued in PCT/FR2009/000848 on Mar. 4, 2010.
Written Opinion of the International Searching Authority (English) issued in PCT/FR2009/000848 on Jan. 11, 2011.
International Preliminary Examination Report issued in PCT/FR2009/000848 on Jan. 11, 2011.

* cited by examiner

% lip max: final lipid content in $g_{lip} \cdot g_x^{-1}$

R S/lip: Substrate-into-lipids conversion yield in $g_{lip} \cdot g_{lc}^{-1}$

P(lip): Volume productivity of lipid production in $g_{lip} \cdot l^{-1} \cdot h^{-1}$

MUTANT YEAST STRAINS CAPABLE OF ACCUMULATING A LARGE QUANTITY OF LIPIDS

CROSS-REFERENCE TO RELATED APPLICATIONS

This application is a U.S. National Stage of international application PCT/FR2009/000848, filed Jul. 8, 2009, which designates the U.S. and which was filed in French and which claims priority to FR0854786, filed Jul. 11, 2008. Each of these applications is incorporated by reference herein in its entirety.

Increased interest in alternative energy has intensified the search for alternative energy sources.

Several technologies, such as large-scale fermentation, have been applied to the industrial production of oil from microorganisms using fats or glycerol as substrates.

Among potential industrial applications of these processes, one of particular interest involves the accumulation within microorganisms of lipids fortified with essential fatty acids; these lipids are intended to be used as nutritional supplements or for fuel production in the form of petroleum-alternative renewable energy.

In light of the growing economic importance of renewable energy sources, interest in improving the composition and oil content of the microorganisms, specifically of yeasts, has increased.

In this regard, the oleaginous yeast *Yarrowia lipolytica* is one of the most widely-studied "nonconventional" yeasts due to its ability to accumulate a large quantity of lipids (approximately 40% of its dry weight).

Yeasts, specifically *Yarrowia lipolytica*, are able to effectively use hydrophobic substrates, e.g., alkanes, fatty acids, and oils, as sole carbon sources.

Ingested aliphatic chains can be used for energy production or can be accumulated in unchanged or modified forms.

Storage molecules such as triglycerides (TG) and/or sterylesters (SE), which are unable to integrate into phospholipid bilayers, group themselves to form the hydrophobic nucleus of said lipid bodies (LB).

Said lipid bodies have long been viewed solely as a means for storing neutral lipids that may be mobilized during periods of deprivation.

However, the image of said lipid bodies as a simple storage compartment has had to be revised since many proteins of said lipid bodies have been identified as enzymes involved in lipid metabolism, specifically in triglyceride synthesis and/or degradation.

In yeasts, triglyceride synthesis follows the Kennedy pathway. Free fatty acids are activated for coenzyme A (CoA) and used to acylate glycerol, on which triglyceride synthesis depends.

In the first step of triglyceride assembly, glycerol-3-phosphate (G-3-P) is acylated by the specific acyltransferase of glycerol-3-phosphate (glycerol-3-phosphate transferase, or SCT1), yielding lysophosphatidic acid, which is then acylated by the specific acyltransferase of lysophosphatidic acid (phosphatidic acid acyltransferase, or SLC1), yielding phosphatidic acid (PA). The latter is then dephosphorylated by a specific phosphohydrolase of phosphatidic acid (phosphatidic acid phosphohydrolase (PAP)) in order to release diacylglycerol (DAG).

In the final step, the diacylglycerol is acylated either by a diacylglycerol acyltransferase or by a diacylglycerol acyltransferase phospholipid in order to produce triglycerides.

Table 1 below describes the genes involved in fatty acid metabolism in yeasts, specifically in *Yarrowia lipolytica* (YL).

TABLE 1

| Gene | Name | EC No. | Function |
| --- | --- | --- | --- |
| GUT1 | YALI0F00484g | EC 2.7.1.30 | Glycerol kinase |
| GPD1 | YALI0B02948g | EC 1.1.1.18 | Glycerol-3-phosphate dehydrogenase (NAD(+)) |
| GUT2 | YALI0B13970g | EC 1.1.99.5 | Glycerol-3-phosphate dehydrogenase |
| SCT1 | YALI0C00209g | EC 2.3.1.15 | Glycerol-3-phosphate acyltransferase |
| SLC1 | YALI0E18964g | EC 2.3.1.51 | 1-acyl-sn-glycerol-3-phosphate acyltransferase |
| DGA1 | YALI0E32769g | EC 2.3.1.20 | Diacylglycerol acyltransferase |
| LRO1 | YALI0E16797g | EC 2.3.1.158 | Phospholipid: diacylglycerol acyltransferase |
| TGL3 | YALI0D17534g | EC 3.1.1.3 | Triacylglycerol lipase |
| TGL4 | YALI0F10010g | EC 3.1.1.3 | Triacylglycerol lipase |
| ARE1 | YALI0F06578g | EC 2.3.1.26 | Acyl-CoA: sterol acyltransferase |
| TGL1 | YALI0E32035g | EC 3.1.1.13 | Cholesterol esterase |
| POX1 | YALI0E32835g | EC 6.2.1.3 | Acyl-coenzyme A oxidase |
| POX2 | YALI0F10857g | EC 6.2.1.3 | Acyl-coenzyme A oxidase |
| POX3 | YALI0D24750g | EC 6.2.1.3 | Acyl-coenzyme A oxidase |
| POX4 | YALI0E27654g | EC 6.2.1.3 | Acyl-coenzyme A oxidase |
| POX5 | YALI0C23859g | EC 6.2.1.3 | Acyl-coenzyme A oxidase |
| POX6 | YALI0E06567g | EC 6.2.1.3 | Acyl-coenzyme A oxidase |
| MFE1 | YALI0E15378g | EC 4.2.1.74 | Multifunctional beta-oxidation protein |
| POT1 | YALI0E18568g | EC 2.3.1.16 | Peroxisomal oxoacyl thiolase |

In yeasts, fatty acid degradation is caused by β-oxidation, a multi-step process that requires four different enzymatic activities.

In yeasts, enzymes are essentially located inside peroxisomes, unlike in mammals, where they are located inside mitochondria and peroxisomes.

The mobilization of accumulated lipids occurs over the course of three distinct phases:

(i) the exponential phase, during which the stored lipid compounds are used to synthesize membrane lipids in order to support cell growth and division, (ii) the stationary phase; when nutrients have become depleted, the free fatty acids are released, quite slowly, from the triglycerides and undergo peroxisomal β-oxidation;

(iii) when the cells are in deprivation conditions, e.g., when finishing the stationary phase and beginning the vegetative growth cycle with carbon supplementation, lipid deposits are very rapidly broken down into free fatty acids.

Over the course of their research, the inventors have focused on the importance of glycerol-3-phosphate (G-3-P) in triglyceride formation.

Glycerol-3-phosphate, located inside lipid inclusions, has already been thought to play a crucial role in triglyceride metabolism.

Two synthesis pathways exist for glycerol-3-phosphate.

In the first, glycerol-3-phosphate is derived from glycerol via glycerol kinase coded by the GUT1 gene.

In the second pathway, glycerol-3-phosphate is directly synthesized from dihydroxyacetone phosphate (DHAP) catalyzed by glycerol-3-phosphate dehydrogenase (coded by the GPD1 gene). The latter reaction is reversible and the formation of DHAP from glycerol-3-phosphate is catalyzed by a second isoform of glycerol-3-phosphate dehydrogenase, whose gene is referred to as GUT2.

In surprising and unexpected fashion, the inventors have, for the first time, shown that lipid accumulation in yeasts, specifically in *Yarrowia lipolytica*, may follow the extinction of the GUT2 gene coding the Gut2p isoform of glycerol-3-phosphate dehydrogenase, and that this extinction may lead to increased lipid accumulation in yeasts, specifically in *Yarrowia lipolytica*.

It should be understood that, in this text, the use of the term "yeast" implies that we are referring to—even if this is not specified—yeast strains in general and, preferably, *Yarrowia lipolytica* yeast strains.

Additionally, the inventors have also shown that a concomitant extinction of the GUT2 gene and of the genes responsible for lipid β-oxidation, e.g., the POX genes, partially (POX2 through POX5) or totally (POX1 through POX6), or the MFE1 gene or the POT1 gene, in order to block the β-oxidation pathway, further increases lipid accumulation in yeasts, specifically in *Yarrowia lipolytica*. In yeasts, specifically in *Yarrowia lipolytica*, 6 genes—POX1, POX2, POX3, POX4, POX5, and POX6—code 6 isoforms of acyl-CoA oxidases that are involved, at least partially, in β-oxidation. The partial or total extinction of the expression of these genes coding these isoenzymes leads to the accumulation by yeasts, specifically by *Yarrowia lipolytica*, of dodecanedioic acid, without consumption of the accumulated lipids.

Based on these discoveries, the inventors are proposing a novel mutant yeast strain, specifically of *Yarrowia lipolytica* yeast, that does not express the GUT2 gene, and a mutant yeast strain, specifically of *Yarrowia lipolytica*, that does not express the GUT2 gene or the genes responsible for lipid β-oxidation, specifically the POX genes (1 through 6), with said mutant strains being able to accumulate a large quantity of lipids.

Disrupting the GUT2 gene (YALI0B13970g) yields mutant yeast strains, specifically of *Yarrowia lipolytica* yeasts, that increase the level of total accumulated lipids and increase the rate of lipid accumulation while growing on glucose and/or on lipids. These mutants are able to produce n-2 fatty acids by partially blocking β-oxidation (a single β-oxidation cycle). Hence, starting with an 18:1 (n-9) fatty acid, we accumulate the product of one β-oxidation cycle, which is 16:1 (n-9), (Z)-7-hexadecenoic acid.

Likewise, the concomitant disruption of the GUT2 gene (YALI0B13970g) and of the genes responsible for lipid β-oxidation, specifically of the POX genes, yields mutant yeasts, specifically of *Yarrowia lipolytica*, that are able to increase the level of total accumulated lipid, to increase the lipid accumulation rate while growing on glucose or on lipid, and with no consumption of the accumulated lipids.

Thus, a goal of the invention is a novel yeast strain, specifically a *Yarrowia lipolytica* strain, that is mutant, that does not express the GUT2 gene, and that is able to accumulate lipids. Preferably, according to the invention, said strain is a JMY1202, |delta|gut2 strain deposited with the National Collection of Microorganism Cultures (CNCM, Pasteur Institute, 25, rue du Docteur Roux, F-75724 Paris Cedex 15) under the CNCM No. 1-4038, on Jul. 8, 2008.

According to a specific mode, a goal of the invention is a novel yeast strain, specifically a *Yarrowia lipolytica* strain, that is mutant, that expresses neither the GUT2 gene nor at least one gene responsible for lipid β-oxidation, and is able to accumulate lipids.

According to another specific mode, a goal of the invention is a novel yeast strain, specifically a *Yarrowia lipolytica* strain, that is mutant, that expresses neither the GUT2 gene nor at least one gene responsible for lipid β-oxidation, that is selected from the POX, MFE1, or POT1 genes, advantageously the POX genes, partially (POX2 through POX5) or totally (POX1 through POX6), and that is able to accumulate lipids.

Preferably according to the invention, said *Yarrowia lipolytica* strain, which is mutant and expresses neither the GUT2 gene nor the POX1, POX2, POX3, POX4, POX5 or POX6 genes; said mutant strain is able to accumulate lipids. Preferably according to the invention, said strain is a JMY1393, |delta|gut2|delta|pox1-6 strain deposited with the National Collection of Microorganism Cultures (CNCM, Pasteur Institute, 25, rue du Docteur Roux, F-75724 Paris Cedex 15) under the CNCM No. 1-4169, on May 28, 2009.

Another goal of the invention is a method for obtaining a mutant yeast strain, specifically a *Yarrowia lipolytica* strain, that is able to accumulate lipids.

The prior art describes various methods for obtaining yeast strains, specifically *Yarrowia lipolytica* strains, that do not express a gene.

For example, we will cite the so-called POP IN/POP OUT method that has been used in yeasts, specifically in *Yarrowia lipolytica*, for deleting LEU2, URA3, and XPR2 genes, as is described in the review by G. Barth et al.: (*Yarrowia lipolytica*, in: Nonconventional Yeasts in Biotechnology: A Handbook (Wolf, K., Ed.), Vol. 1, 1996, pp. 313-388. Springer-Verlag). It consists of integrating a vector comprising a deleted gene of interest into the relevant locus, then of selecting the excision of said vector and of identifying a clone that, via cross-over eliminates the wild type gene and preserves the mutated gene.

Preferably according to the invention, a method resulting in the disruption of the gene of interest may be used.

By "disruption of the gene of interest," we mean, according to the invention, any method resulting in the nonexpression of the native protein coded by said gene of interest, by modifying the nucleotide chain constituting said gene in such a way that, even if its translation were to be effective, it would not lead to the expression of the native protein coded by the wild type gene of interest.

Preferably according to the invention, a method resulting in total extinction of expression of the gene of interest is used. This may be carried out via a total deletion of the gene of interest, by a partial deletion of the gene of interest, [or] by inserting one or several nucleotides into said gene of interest, with said method used rendering the gene of interest nonfunctional (disrupted gene of interest), at the very least coding a protein that does not have the properties of said native protein. We thereby obtain a yeast strain that does not express the gene of interest, which we will refer to hereinafter as the "gene-of-interest-defective strain."

One may thus use the SEP method (Maftahi M., et al.; Yeast 12: 859-868) that was adapted in *Yarrowia lipolytica* for the successive disruption of POX genes (Wang H. J. et al., 1999; J. Bacteriol., 181:5140-5148). Advantageously according to the invention, the SEP/cre method developed by Fickers et al.

(2003, J. Microbiol. Methods 55/3: 727-737) and described in international patent application WO2006/064131 will be used. It is a rapid method that does not require the use of a marker enabling a counterselection.

In summary, this method consists in:

1) selecting a yeast gene of interest, specifically a *Yarrowia lipolytica* gene, whose expression is to be suppressed either by deleting the gene or at least by disrupting it:

2) constructing a disruption cassette via polymerase chain reaction (PCR) or via cloning, including the promoter (P) and terminator (T) sequences of the gene of interest, flanking a gene coding a selection marker (selection gene), with said selection gene itself being flanked on either side of its sequence by one or more cross-over sequence(s), with said cross-over sequences enabling cross-over between themselves that results in the elimination of said gene coding the selection marker;

3) introducing said disruption cassette obtained in 2) into a yeast strain;

4) selecting a gene-of-interest-defective yeast strain that has introduced, via double cross-over, the marker gene in lieu of the gene of interest, thereby leading to an disrupted gene of interest;

5) verifying the disruption of said gene of interest inside said gene-of-interest-defective yeast strain selected in Step 4, and optionally 6) transforming said strain selected in Step 5 with a vector enabling the expression of a recombinase in order to obtain the elimination of the gene expressing the selection marker;

7) isolating a gene-of-interest-defective yeast strain, with the recombinase expression plasmid being lost.

Advantageously, in Step 2, the reading frame of the gene of interest is replaced by inserting a marker gene that is itself flanked by repeated sequences enabling a cross-over that may lead to elimination of the marker gene. Advantageously, the cross-over sequence(s) is (or are) one (or more) loxP sequence(s) or one (or more) loxR sequence(s) or one or more sequence(s) derived from these cross-over sequences, with said derived sequence(s) having preserved the activity of the original cross-over sequences.

Preferably in Step 2, the gene coding the selection marker may be flanked by loxP-type sequences that, under the activity of cre recombinase, recombine among themselves and create a plasmid that includes the sequence of the gene coding said selection marker.

Step 3 can be performed using any known yeast transformation method of the prior art. Advantageously, as regards yeast strain culturing, as well as for all usable molecular biology techniques according to the invention, one should consult reference manuals on the topic, namely Sambrook (Sambrook, J., T. Maniatis and E. F. Fritsch, Molecular Cloning: A Laboratory Manual. $2^{nd}$ ed. 1989, Cold Spring Harbor, N.Y.: Cold Spring Harbor Laboratory Press) or Barth (Barth, G. and C. Gaillardin, Nonconventional Yeasts in Biotechnology, W. K., Editor. 1996, Springer-Verlag: Berlin, Heidelberg, N.Y. Pp. 313-388).

Step 4 of the method consists of selecting transformed yeast strains that express the selection marker.

Step 5 can be performed using any known method and, specifically, using PCR according to the technique developed by Gussow et al. (Nucleic Acids Res. 17, 1989, 4000), then confirmed by Southern blot hybridization.

Step 6 can be performed as per Step 3. Advantageously, a plasmid carrying the gene coding cre recombinase will be used (Sauer, B. (1978), Mol. Cell. Biol., 7, 2087-2096) that enables the cross-over of loxP/loxR sequences and elimination of the marker. This technique is well-known in the prior art (Hoess, R. and Abremski, K. (1984) J. Mol. Biol., 181, 351-362).

Step 7 is a standard step in any mutant selection method that consists in isolating a clone selected by successive subculturing until a pure strain is obtained.

Specifically, a goal of the invention is a method for obtaining a yeast strain, specifically a *Yarrowia lipolytica* strain, that is mutant and that does not express the GUT2 gene, wherein in a first step, a disruption cassette is constructed that includes the promoter and terminator sequences of the GUT2 yeast gene (SEQ ID No. 1), specifically of *Yarrowia lipolytica*, flanking a gene coding a selection marker (selection gene), with said selection gene itself being flanked on either side of its sequence by one (or more) cross-over sequence(s), with said cross-over sequences enabling a cross-over among themselves resulting in the elimination of said gene coding the selection marker;

in a second step, said disruption cassette obtained in Step 1 is introduced into a yeast strain, specifically a *Yarrowia lipolytica* strain;

in a third step, one selects, from among the yeast strains transformed in Step 2, a yeast strain, specifically a *Yarrowia lipolytica* strain, that is defective for the GUT2 gene, with the strain having introduced via double cross-over the marker gene in lieu of the GUT2 gene, thereby leading to a disrupted GUT2 gene (gut2::URA3 strain);

in a fourth step, the disruption of said GUT2 gene in said yeast strain selected in Step 3 is verified.

According to one variation on the invention, the method may involve 2 additional steps, namely:

a fifth step, during which said strain selected in Step 4 is transformed with a vector enabling the expression of a recombinase in order to eliminate the gene expressing the selection marker;

a sixth step, during which a yeast strain defective for the GUT2 gene, and no longer expressing the marker gene, referred to as ☐gut2, is isolated.

According to the invention, during the first step of the method, one constructs said disruption cassette including the promoter and terminator sequences of the GUT2 yeast gene, specifically of the *Yarrowia lipolytica* strain, according to the technique described by Fickers et al. (2003, J. Microbiol. Methods 55/3:727-737). To do this:

one first synthesizes, using PCR for example, and purifies DNA fragments including either the Promoter (P) sequence or the Terminator (T) sequence of the GUT2 yeast gene, specifically of *Yarrowia lipolytica*, advantageously a wild type yeast strain, even more advantageously an already-purified W29 strain of *Yarrowia lipolytica*. When these fragments are synthesized using PCR, one may use any compatible primer pair, specifically with the DNA of *Yarrowia lipolytica*, the pairs G3P-P1/G3P-P2 (SEQ ID Nos. 2 and 3) for the P part and G3P-T1/G3P-T2 (SEQ ID Nos. 4 and 5) for the T part. Advantageously, the G3P-P2 and G3P-T1 primers may each additionally comprise a restriction site sequence, preferably a rare site such as, for example, a site selected from among the meganucleases (Homing endonucleases) such as I-Ceul, I-Scel, PI-Pspl, PI-Scel, preferably the I-Scel site;

secondly, using any known method in molecular biology, one brings together a P fragment and a T fragment, advantageously via the restriction site, advantageously the I-SceI site, to form P-site rare-T DNA fragments (referred to as disruption cassettes 2 or GUT2-PT disruption cassettes);

thirdly, one introduces into the restriction site of disruption cassette 2 a gene coding a selection marker, e.g., a gene associated with an auxotrophy phenotype or of dominant character; as auxotrophy markers, we will cite by way of example URA3, LEU2, ADE2, HIS and LYS5. As dominant markers, we will cite antibiotics-resistant genes, preferably the hygromycin resistance gene (HYG), preferably a gene coding URA3, LEU2, ADE2, HYG, to form P-I-Sce I-Marker-I-Sce I-T DNA fragments (referred to as disruption cassette 1 or as GUT2-PUT disruption cassette when the marker gene is the URA3 gene, disruption cassette GUT2-PLT when the marker gene is the LEU2 gene).

fourthly, said disruption cassette is purified either through digestion of the GUT2-PUT or GUT2-PLT plasmid by appropriately using restriction enzymes on either side of the disruption cassette, or through PCR with the P1 and T1 primers.

According to the invention, in the second step of the method, the disruption cassette 1 obtained in the first step is introduced into a yeast strain, specifically a wild type *Yarrowia lipolytica* strain such as, for example, a W29 strain, or advantageously a yeast strain, specifically a *Yarrowia lipolytica* strain, that does not express the selection marker gene contained in the disruption cassette, such as, for example, a Po1d strain, which is a strain that is auxotrophic for leucine (Leu−) and uracil (Ura−) described by G. Barth et al. (Non-conventional Yeasts in Biotechnology: A Handbook (Wolf, K. Ed.), Vol. 1, 1996, pp. 313-388. Springer-Verlag, Berlin, Heidelberg, N.Y.) and listed under the reference CLIB139 in the collection of the CIRM (International Center for Microbial Resources, previously titled the Collection of Yeasts of Biological Interest (CLIB), or the JMY1202 strain (Leu−, Ura+, Δgut2PUT)] obtained via complementation of the Ura− defection of the Po1d strain by transforming the Po1d strain with the GUT2-PUT disruption cassette or of the JMY1387 strain (Leu+, Ura+, Δgut2PUT)] obtained via complementation of the Leu− defection of the JMY1202 strain by transforming the JMY1202 strain with a DNA fragment containing the LEU2 gene.

Even more advantageously in this step, one may use a yeast strain that will not perform lipid β-oxidation, e.g., a strain that will not express the genes responsible for lipid β-oxidation such as the POX, MFE1, OR POT1 genes, advantageously a strain that does not express the POX genes, at the very least the POX2, POX3, POX4, and POX5 genes, preferably the POX1, POX2, POX3, POX4, POX5, and POX6 genes, such as, for example, the strains described in the international patent application WO 2006/064131 published on Jun. 22, 2006, preferably the strains MTLY37 (Leu+, Ura+; Δpox5, Δpox2, Δpox3, Δpox4::URA3), MTLY40 (Leu+, Ura−; Δpox5-PT, Δpox2-PT, Δpox3-PT, Δpox4::ura3-41), MTLY64 (Leu−, Ura−, Hyg+; Δpox5, Δpox2, Δpox3, Δpox4::ura3-41, leu2::Hyg), MTLY66 (Leu−, Ura−; Δpox5, Δpox2, Δpox3, Δpox4::ura3-41, Δleu2), MTLY82 (Leu−, Ura−, Hyg+; Δpox5, Δpox2, Δpox3, Δpox4::ura3-41, Δleu2, pox1::Hyg), MTLY85 (Leu−, Ura−; Δpox5, Δpox2, Δpox3, Δpox4::ura3-41, Δleu2, Δpox1), MTLY92 (Leu−, Ura−, Hyg+; Δpox5, Δpox2, Δpox3, Δpox4::ura3-41, Δleu2, Δpox1, pox6::Hyg), MTLY95a (Leu−, Ura−; Δpox5, Δpox2, Δpox3, Δpox4::ura3-41, Δleu2, Δpox1, Δpox6).

In this step, any known transfer method of the prior art (see "Sambrook") can be used to introduce disruption cassette 1 into the yeast strain. Preferably, one may use the lithium acetate and polyethylene glycol method described by Gaillardin et al. (Curr. Genet. 11, 1987, 369-375).

According to the invention, in the third step, it is possible to use any known selection method of the prior art that is compatible with the marker gene (or genes) used, with any strain expressing the selected marker gene being potentially a yeast strain that is defective in the GUT2, URA3, or LEU2 gene.

According to the invention, in the fourth step, the disruption of said GUT2 gene in said yeast strain selected in the third step is verified, using any compatible method described in the prior art, preferably using PCR according to the technique of Gussow et al. (Nucleic Acids Res. 17, 1989, 4000), then optionally confirmed by Southern blot hybridization (Sambrook).

The mutant strains obtained in this step, which are able to accumulate lipids, express the selection marker. However, it may be necessary to possess mutant strains that are able to accumulate lipids but that do not express the selection marker. Hence, the method of the invention may also include a fifth and a sixth step for obtaining such mutant strains that are able to accumulate lipids but that do not express the selection marker.

According to the invention, in the fifth step, the strain selected in the fourth step is transformed with a vector enabling the expression of a recombinase in order to eliminate the gene expressing the selection marker. By way of example, it is possible to introduce a replicative vector enabling the expression of cre recombinase and possessing the LEU2 selection marker, such as the pRRQ2 vector (Fickers, op. cit.);

According to the invention, in the sixth step, one isolates a yeast strain that is defective in the GUT2 gene and that no longer expresses the marker gene used to invalidate the GUT2 gene, and that has optionally lost the replicative plasmid enabling recombinase expression, using any known selection or isolation method of the prior art, such as, for example, culturing in rich medium or spreading on rich medium, which no longer makes it possible to select for the selection marker.

Another goal of the invention is the use of a yeast strain, specifically a *Yarrowia lipolytica* strain, that is mutant and able to accumulate lipids, e.g., a strain of the invention, in order to synthesize lipids, specifically free fatty acids and triacylglycerols. Preferably, according to the invention, one will use a *Yarrowia lipolytica* strain that is mutant and able to accumulate lipids, advantageously a strain that no longer expresses the GUT2 gene (Δgut 2 strain), preferably the JMY1202 strain (CNCM 1-4038), even more preferably a strain that no longer expresses the GUT2 or the POX genes, very advantageously the JMY1393 strain (CNCM 1-4169). Advantageously according to the invention, the mutant strains may be used to produce n-2 fatty acids, very advantageously to produce 16:1 (n-9), (Z)-7-hexadecenoic acid.

Another goal of the invention is a method for synthesizing lipids, wherein:

in a first step, one grows, in an appropriate medium, a yeast strain, specifically a *Yarrowia lipolytica* strain, that is mutant and able to accumulate lipids, e.g., a strain of the invention;

in a second step, the lipids produced by the culturing in Step 1 are collected.

Along with the preceding features, this invention also includes other characteristics and advantages that will be more fully understood through the following examples and figures, which should be understood to illustrate the invention without limiting its scope.

FIG. 1 shows a diagram for constructing mutant yeasts that do not express a gene of interest, here the GUT2 gene of *Yarrowia lipolytica*, via disruption using a marker gene.
- □: Yeast gene of interest
- —: Yeast genome
- ▬: Rare restriction site (I-Sce 1)
- ▩: Repeated sequences
- ▤: Marker gene
    - P: Promoter sequences of gene of interest
    - T: Terminator sequences of gene of interest
    - G3P-P1, G3P-P2, G3P-T1, G3P-T2: Primers for synthesizing P and/or T fragments by PCR;
    - Ver1, ver2: Primers for verifying disruption by PCR;
    - (1) and (2): synthesis of P and T fragments with insertion of a rare site at the ends
    - (3): P-site rare-T fragment, after fusion of fragments by PCR;
    - (4): insertion of the marker gene at the rare site flanked by: cross-over sequences in order to obtain the disruption cassette;
    - (5): after transformation of the strain, double cross-over between the disruption cassette and the yeast genome;
    - (6): result of the double cross-over: replacement of the reading frame of the gene of interest by the marker gene;
    - (7): gene of interest disrupted in the yeast strain following excision of the marker gene by cross-over.

The strains were grown on YNBD, YNBD$_{0.5}$O$_3$, and ultrapure YNBD$_{0.5}$O$_3$ media.

The results show the average values for three independent experiments.
- ▦: Wild-type strain
- □: Δgut2 strain
- ■: Δgut2Δpox1-6 strain
- u.p.: ultrapure oleic acid (>98% purity)

Figure 1:
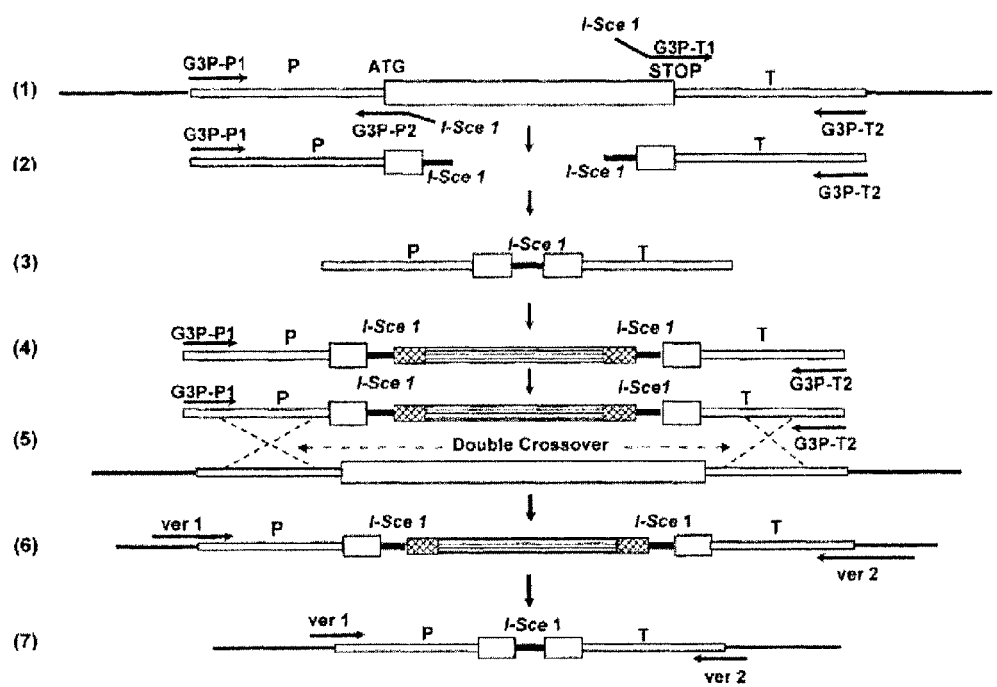
Figure 2:
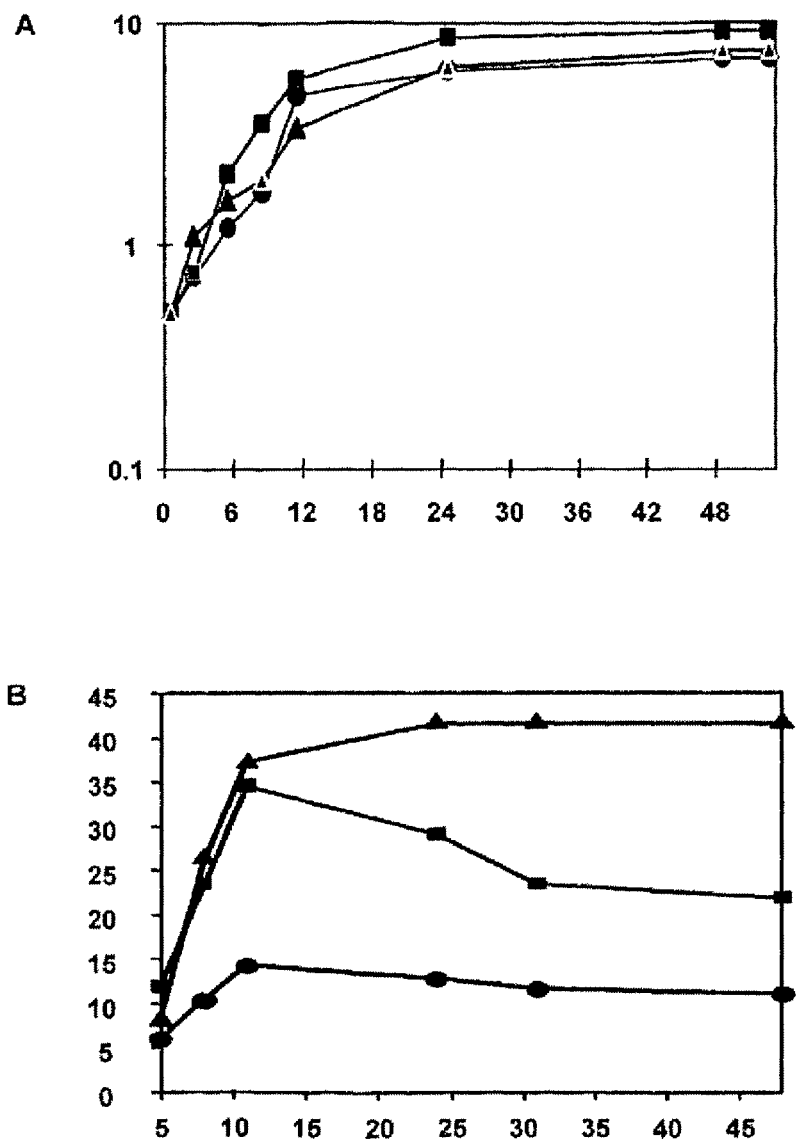
FIG. 2 shows, at A, the growth of wild type strains and of mutant strains (O.D. 600 nm) over time (h), and at B, the total accumulation of fatty acid, expressed as a dry weight percentage of the biomass over time (h).
- ○: wild type strain; □: Δgut2 mutant strain; Δ: Δgut2 Δpox1-6 mutant strain The results are the average values for three independent experiments.
Figure 3:
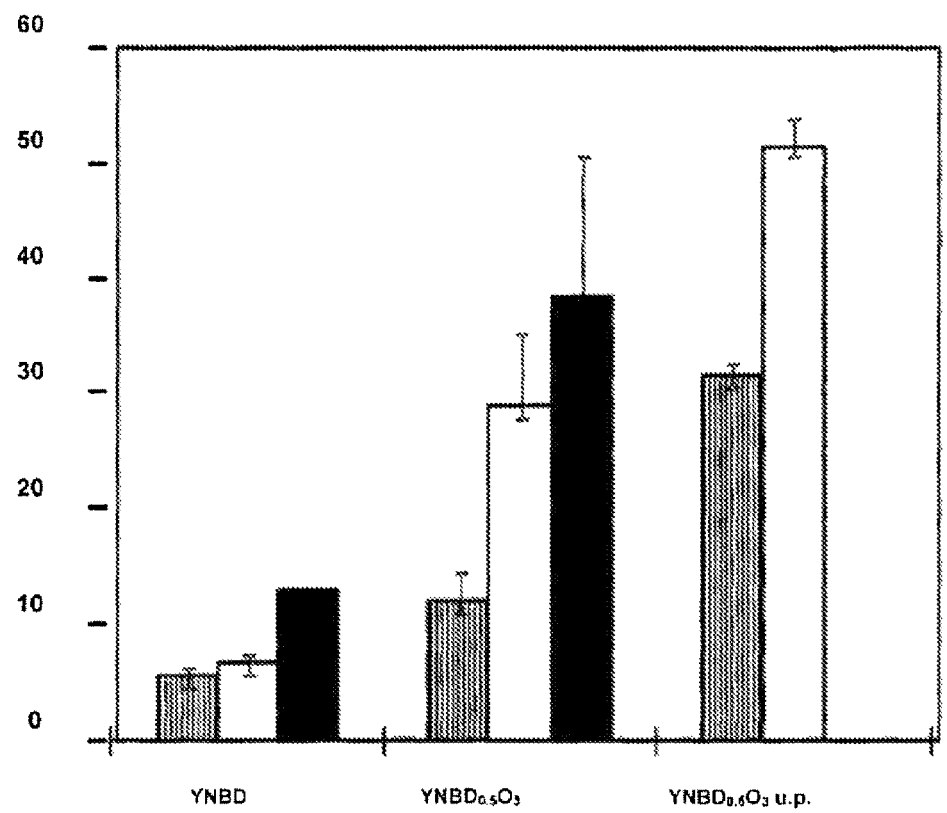
FIG. 3 shows the total amount of fatty acids for the wild type strains and the mutant strains in dry weight percentage of the biomass at the end of cell culturing (24 hrs.).
Figure 4:
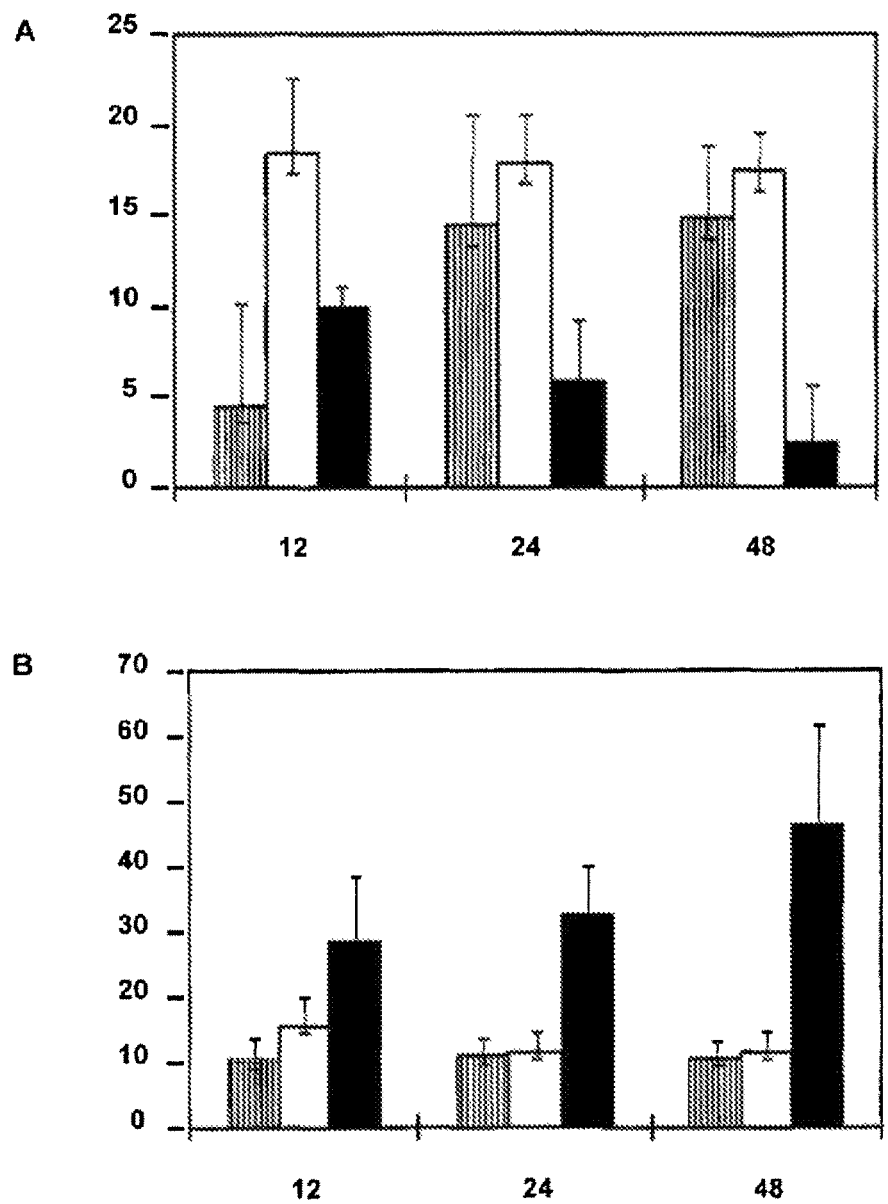

FIG. 4 shows, in Part A, the average number of lipid bodies over time in a wild type strain and in mutant strains, and, in Part B, the percentage of cell surface area covered by the lipid bodies.

Figure 5:
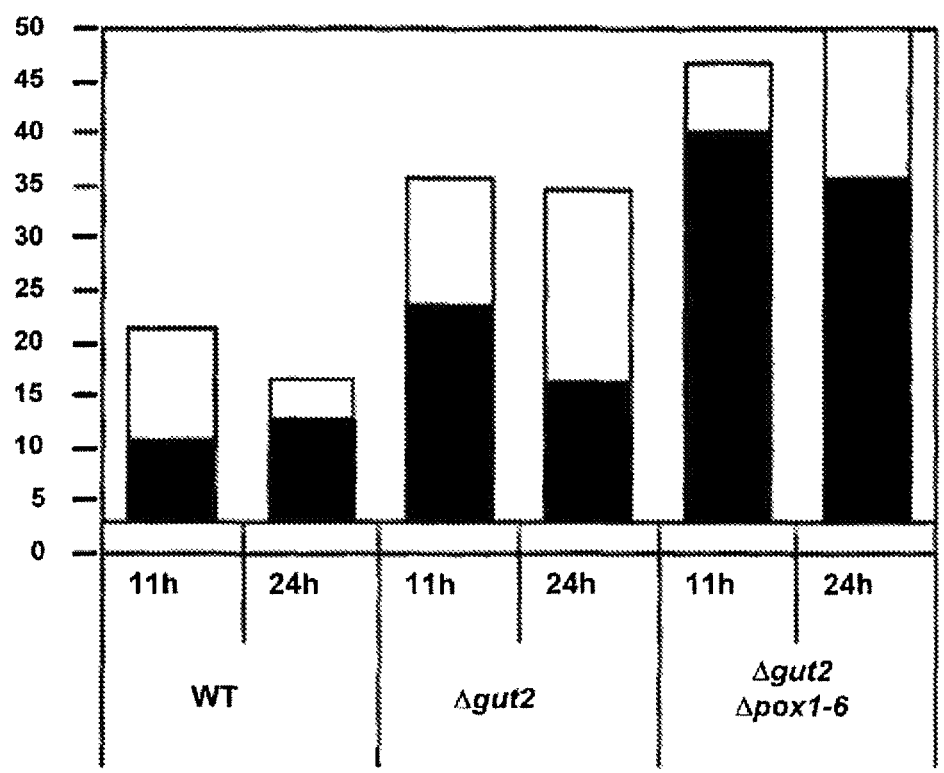
Figure 6:
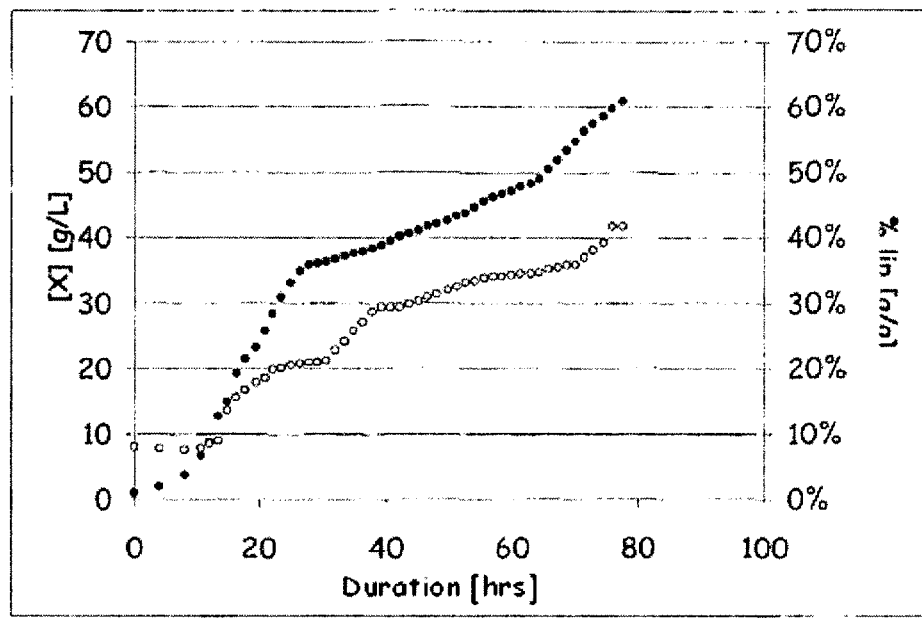

The strains were grown on YNBD$_{0.5}$O$_3$.
- ▦: Wild-type strain
- □: Δgut2 strain
- ■: Δgut2Δpox1-6 strain FIG. 5 shows the total lipid accumulation in the form of dry weight percentages of the biomass over time (11 hrs. and 24 hrs.), separated into triacylglycerols and free fatty acids after growing on the YP$_2$D$_4$O$_3$ medium.
- ■: Free fatty acids
- □: Triacylglycerols FIG. 6 shows the evolution of the biomass (●) and of the percentage of lipids (○) produced over time while culturing the W29 wild type yeast.

Figure 7:
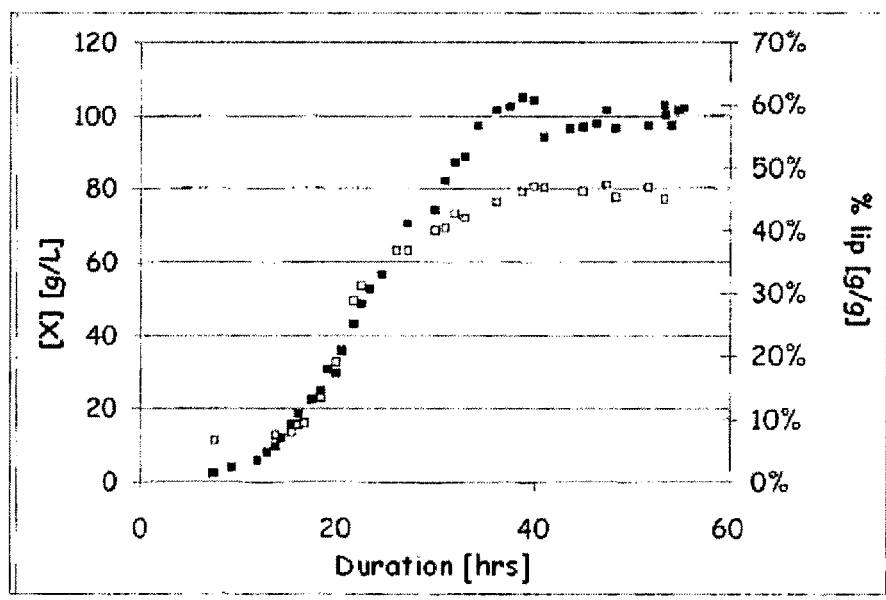

FIG. 7 shows the evolution of the biomass (■) and of the percentage of lipids (□) produced over time while culturing the Δgut2 mutant strain.

Figure 8:
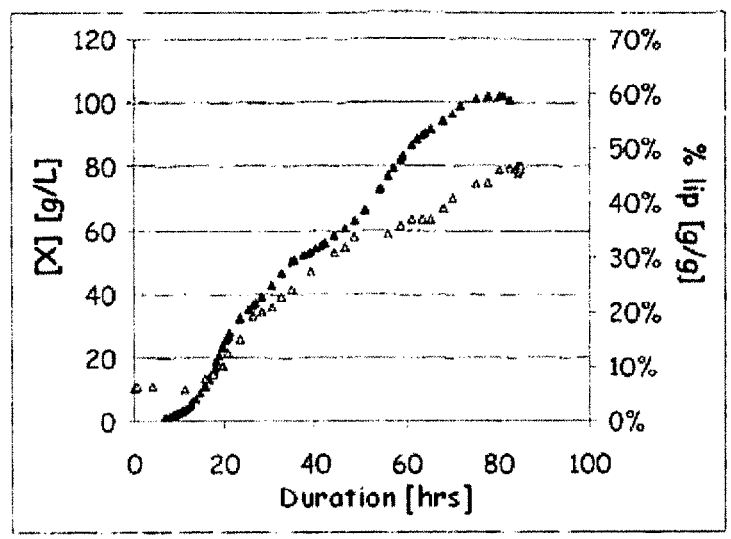

FIG. 8 shows the evolution of the biomass (▲) and of the percentage of lipids (Δ) produced over time while culturing the Δgut2Δpox1-6 mutant strain.

Figure 9:
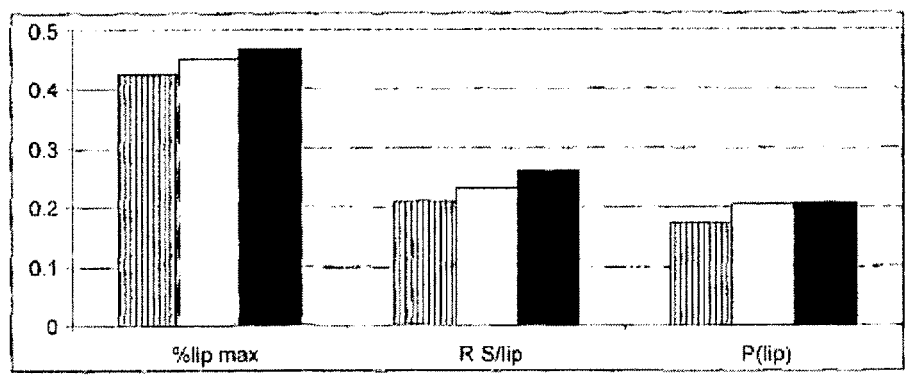

FIG. 9 shows the comparative assessment of the strain cultures
- ▦: W29 wild type
- □: Δgut2 mutant
- ■: Δgut2Δpox1-6 mutant according to:
- % max lip: final amount of lipids expressed in $g_{lip}g^{-1}$
- R S/lipY: substrate-into-lipid conversion yield in $g_{lip} \cdot g_{glc}^{-1}$
- P(lip): volume productivity of lipid production in $g_{lip} \cdot l^{-1} \cdot h^{-1}$.

EXAMPLES

Material and Methods

Yeast Strains and Culture Conditions

The *Y. lipolytica* strains used are derived from the wild type *Y. lipolytica* strain, W29 (ATCC 20460).

The auxotrophic Po1d (Leu−, Ura−) strain was described previously by Barth and Gaillardin [Nonconventional Yeasts in Biotechnology, W. K., Editor. 1996, Springer-Verlag: Berlin, Heidelberg, N.Y. Pp. 313-388)].

The prototrophic MTLY37 strain, which contains a disruption of the four POX genes coding for four acyl-CoA oxidases (AOX), was described by Wang and colleagues (Wang, H. J., et al., J Bacteriol, 1999. 181(17): pp. 5140-5148).

The auxotrophic MLTY40 (Ura−) strain were [sic] obtained by transforming MLTY37, using a 1.5 kb fragment carrying the ura3-41 allele, obtained by PCR, followed by selecting transformants on YNB-5FOA medium (Mlickova, K., et al., Appl Environ Microbiol, 2004. 70(7): pp. 3918-3924).

Culture Medium and Growing Conditions

For *E. coli*, the conditions are described in Sambrook and in Barth for *Y. lipolytica* (op. cit).

The YPD rich medium, the YNB minimal glucose medium, and the YNBcas casamino-acid-supplemented minimal medium were prepared as described previously by Mlickova, K., et al. (op. cit.) Appl. Environ. Microbiol., 2004. 70(7): pp. 3918-3924.

The YNB minimal medium contains 0.17% YNBww (YNB medium without amino acids or ammonium sulfate; Difco, Paris, France), 0.5% NH$_4$Cl, 0.1% yeast extract (Bacto-DB), and 50 mM 6.8-pH phosphate buffer.

The carbon-source-supplemented media are:
- YNBD medium (2% glucose, Merck, Fontenay-sous-Bois Cedex, France);
- TNBG medium (2% glycerol, Merck);
- YNBDO medium (medium supplemented with 3% of 60%-pure Merck oleic acid);
- NBDOu.p. medium (medium supplemented with 3% of 98%-pure Flucka oleic acid);
- the YNBO (YNBD$_{0.5}$O$_3$) medium used for monitoring optimal fatty acid accumulation and remobilization is the YNB medium supplemented with 0.5% glucose and 3% oleic acid;
- the YP$_2$D$_4$O$_3$ medium used for optimizing lipid accumulation contains yeast extract (1%), proteose peptone (2%), glucose (4%), and oleic acid (3%).

Uracil (0.1 g/L) and leucine (0.2 g/L) were added as needed.

For solid media, 1.5% of agar was added.

The oleic acid was emulsified by sonication in the presence of 0.02% Tween 40 (Mlickova, K., et al. (Appl. Environ. Microbiol., 2004. 70(7): pp. 3918-3924).

As a general rule, the cultures were created as follows:

Starting with a YPD dish, an initial preculture was inoculated in YPD medium (15 ml in 50-ml Erlenmeyer flasks at 170 rev./min., at 28° C. for 6 hrs). The cells were used to inoculate a preculture in YNBD medium (50 ml in a 500-ml Erlenmeyer flask at 170 rev./min., at 28° C., overnight).

For the culture, exponential-growth cells were collected by centrifugation on the day following preculture and resuspended in fresh YNB medium at an optical density of 0.5 at 600 nm.

In order to determine cell growth, the cultures were centrifuged at 10000×g for 10 min., and the cell pellet was washed twice with equal volumes of SB solution (9 g/L of NaCl-0.5% BSA).

The produced biomass was determined by measuring the optical density at 600 nm and by estimating the dry weight of the cells after being heated to 80° C. for 24 hrs.

General Genetics Techniques

General molecular genetics techniques were used as described in Sambrook.

The restriction enzymes came from Eurogentec SA (Liège, Belgium).

The yeast genomic DNA (wild type or transformed) was prepared as described by Querol et al. (Appl. Environ. Microbiol., 1992. 58(9): pp. 2948-2953).

The PCR amplifications were performed on an Eppendorf 2720 thermal cycler, with either Taq DNA polymerase (Promega, Madison, Wis., USA) or with Pfu DNA polymerase (STRATAGENE, La Jolla, Calif.).

Table 2 below describes the usable primers of the invention:

TABLE 2

| Primers | SEQ ID No. | Sequence (5' → 3')[a] | Restriction site, introduced |
|---|---|---|---|
| G3P-P1 | 2 | GCAGATCCACTGTCAAGCCG | |
| G3P-P2 | 3 | GCTAGGATAACAGGGTAATGCGGTAGGAA AGAGAAGTTCCGCG | I-SceI |
| G3P-T1 | 4 | GCATTACCCTGTTATCCCTAGCCGGACTATTT CCCCGCAGC | I-SceI |
| G3P-T2 | 5 | GCAGCCAGCAGCACGTAGTAG | |
| G3P-ver1 | 6 | GAATGACGGGGCAACGCAG | |
| G3P-ver2 | 7 | CAGCAGCCACAAATAGCAGACTGCC | |
| Leu2-P1 | 8 | AATCTAGATGGTCACAGTGGAATCATGTTCG TGG | XbaI |
| LEU2-P2 | 9 | CATTACCCTGTTATCCCTAGGTTCCATTGTGG ATGTGTGTGGTTG | I-SceI |
| LEU2-T1 | 10 | CTAGGGATAACAGGGTAATGCTCTGGGTCTG CTGCCCTC | I-SceI |
| LEU2-T2 | 11 | AGTAAGCTTAGATCTGTTCGGAAATCAACGG ATGCTAACC | HindIII |
| POX1-P1 | 12 | CATGGAGTGGATCGCTCGAGGACG | |
| POX1-P2 | 13 | GCATTACCCTGTTATCCCTAGCCAGGAGGAT CGGTGAATGTG | I-SceI |
| POX1-T1 | 14 | GCTAGGGATAACAGGGTAATGCCTTGTTCCG AGAAGAGGAGGACG | I-SceI |
| POX1-T2 | 15 | CGGCAGTGGCTCACCAAGC | |
| POX1ver1 | 16 | ATCCAGACCTCCAGGCGGG | |
| POX1ver2 | 17 | GCTGCGTCTCAATCTGGCGAATG | |
| POX6-P1 | 18 | CCAAGCTCTAAGATCATGGGGATCCAAG | |
| POX-P2 | 19 | GCATTACCCTGTTATCCCTAGCGTTGAGGGA CTGTTGAGAGAG | I-SceI |
| POX6-T1 | 20 | GCTAGGGATAACAGGGTAATGCGATGAGGA AATTTGCTCTCTTGAGG | I-SceI |
| POX6-T2 | 21 | ATCTCGAGATTGTCCCCTCAAACACAC | |
| POX6Ver1 | 22 | GCTCAAGAAGGTAGCTGAGTC | |
| POX6ver2 | 23 | CATTAAGTGTCAGATCAGCTCGC | |

[a] the underlined sequences correspond to introduced restriction sites.

The P1, P2, T1, and T2 primers are used to construct disruption cassettes. The ver1 and ver2 primers are used to verify gene disruption by PCR.

The PCR fragments were purified using a QIAGEN purification kit (Qiagen, Hilden, Germany) and the DNA fragments were recovered from agarose gels by using a QIAquick Gel Extraction kit (Qiagen, Hilden, Germany).

The Staden program package (Dear, S, and Staden, R. A Sequence Assembly and Editing Program for Efficient Management of Large Projects. Nucleic Acid Res. 19, 3907-3911 (1991)) was used for sequence analysis.

Yeast cell transformation was performed using the lithium acetate method described in Le Dall, M. T. et al. (Curr Genet, 1994, 26(1): pp. 38-44).

Suppression of the GUT2, LEU2, POX1 or POX6 Genes, Expression of Cre Recombinase, and Marker Excision The suppression cassettes were generated via PCR amplification according to Fickers et al. (op. cit.) (J. Microbiol. Methods, 2003, vol. 55, issue 3, pp. 727-737).

The PT fragment was cloned in the PCR4 RBlunt-TOPO plasmid (TOPO-pCR4 vector; Invitrogen Corp., Carlsbad, Calif.) to obtain a first plasmid named JME743.

The URA3 marker was then introduced at the I-SceI site of the JME743 plasmid to obtain a second plasmid named JME744 containing the gut2-PUT disruption cassette.

For the LEU2 gene, the primer pairs LEU2-P1/LEU2-P2 (SEQ ID No. 8 and 9) and LEU2-T1/LEU2-T2 (SEQ ID No. 10 and 11) were used. P1 was designed to put in place an XbaI restriction site at the 5' end of the P fragment, whereas T2 was designed to put in place a HindIII restriction site.

Following PCR amplification, the PT fragment was digested by XbaI and HindIII and cloned at the corresponding sites of the pDRIVE plasmid (Qiagen, Les Ulis, France) to obtain a third plasmid named JME641. Next, the HPH(HYG) marker was introduced to obtain a fourth plasmid named JME651. The HPH(HYG) marker, originally from an *Escherichia coli* plasmid, enables Hygromycin B resistance (GRITZ & DAVIES, Yeast, vol. 8, pp. 667-668, 1992).

For the POX1 or POX6 genes, the PT sequences were amplified along with their respective primer pairs POXn-P1/POXn-P2 and POXn-T1/POXn-T2 (see Table 2) and blunt-end cloned into the Bluescript KS* plasmid (STRATAGENE).

Following transformation in *E. coli* DH5α and culturing on LB Agar Xgal, white colonies were selected.

The MTLE34 and MTLE35 strains contained the POX1-PT and POX6-PT cassette-carrying plasmids, respectively.

The MTLE36 and MTLE37 strains contained the POX1-PHT and POX2-PHT plasmids, respectively.

The disruption cassettes (PUT and PHT), obtained via PCR, were used for transformation by the lithium acetate method. The transformants were selected on YNBcasa and YPDH medium, respectively.

Disruption was verified via PCR by using ver1/ver2 primer pairs (see Table 2) and excision of the marker gene was performed as per Fickers et al. (op. cit.) (J. Microbiol. Methods, 2003, vol. 55, issue 3, pp. 727-737).

Optical Microscopy

For the optical microscopy experiments, 10 mL of a growing yeast culture was prefixed using 1.34 ml of formaldehyde solution (50 mM phosphate buffer, pH 6.8; 0.5 mM $MgCl_2$; 4.8% formaldehyde) and incubated for 1 hr. at 28° C. while stirring at 250 rev./min. The prefixed cells were collected, placed back in suspension at an optical density of 2.5 at 600 nm in the formaldehyde solution and incubated for 5 hrs. at ambient temperature. Next, the cells were washed twice with 50 mM phosphate buffer (pH 6.8) and stored in 0.1 M phosphate buffer (pH 7.5) at an optical density of 2.5 at 600 nm at 4° C. until optical microscopy observation took place.

Fluorescence Microscopy

For lipid body visualization, Nile red stain (1 mg/ml solution in acetone; Bioprobe moléculaire, Montluçon, France) was added to the cell suspension (1/10 v/v) and followed by 1 hr. of incubation at ambient temperature.

The cells were collected, washed twice with distilled water, and placed back in suspension in 50 mM phosphate buffer (pH 6.8) at an optical density of 2.5 at 600 nm. The examination was performed using an Olympus BX 51 optical microscope with a ×100 lens in an oil bath. For image recording, the Photometrics CooISNAP 2048×2048 element array, 7.4×7.4-μm pixel pitch software program (Roper Scientific, Inc. Photometrics, PVCAM) was used.

Lipid Determination

Lipids from a culture with an optical density equivalent to 10 OD were either extracted by using the procedure developed by Folch et al. (Folch, J. et al., J Biol Chem, 1957. 226(1): pp. 497-509) for TLC analysis or were directly converted into their methyl esters by using lyophilized cells as per Browse, J., et al. (Anal Biochem, 1986. 152(1): pp. 141-5) for gas-phase chromatography analysis.

The complete transmethylation was verified by using a method involving $BF_3$ in methanol (Athenstaedt, J., et al., J Bacteriol, 1999. 181(20): pp. 6441-8) and on TLC plates.

Analysis of the fatty acid methyl esters using gas-phase chromatography was conducted using a Varian 3900 equipped with a flame ionization detector and a Varian FactorFour vf-23 ms column (3pA at 260° C. [30 m, 0.25, 0.25 μm]).

The fatty acids were identified by comparing them to standardized fatty acid methyl esters (Fatty Acid Methyl Ester, FAME, Cayman, Supelco, Sigma (France)) and quantified using the internal standard method by adding 50 μg of commercial C17:0 (Sigma).

Lipid Class Analysis

The total lipids were fractionated into triacylglycerol and free fatty acids for lipid quantification by using an solute SPE Aminopropyl column (IST, France, Paris, France). Column conditioning was performed 3 times with 3 ml of normal hexane at a normal flow rate. 1 ml of all of the lipids extracted using Folch's method in $CHCl_3$ was loaded into the column and the neutral lipid fraction was collected.

Total elution of the neutral lipids was performed by washing the column 3 times with 3 ml of $CHCl_3$/Isopropanol (2/1). The free fatty acid fraction was collected by washing the column 3 times with 3 ml of $ET_2O$/2% acetic acid with a normal flow rate. The fraction solvent was evaporated under a direct nitrogen flux and the transmethylation was monitored for gas-phase chromatography analysis (Laffargue, A. et al., Plant Physiol Biochem, 2007. 45(3-4): pp. 250-7).

TLC plates were used for verification extractions. The procedure's efficacy was also verified by comparing the gas-phase chromatography profiles of fractionated and nonfractionated samples.

Lipid Separation Using TLC

TLC plates (silica G60, 20*20 cm, 0.25 mm thick) (Merck, Germany) were used. The various lipid classes were separated by using a double-development solvent system: System A (one-half of migration plate): petroleum ether/ethyl ether/acetic acid: 20/20/0.8 (v/v/v); System B (entire migration plate) petroleum ether/$Et_2O$ 49/1 (v/v). The plates were dusted with a 5% solution of phosphomolybdic acid and the lipid bands were revealed after 10 min at 105° C.

Example 1

Obtaining the Δgut2 Mutant Strain

Preparing the Genomic DNA of the Wild Type *Yarrowia lipolytica* W29 Strain

The wild type *Yarrowia lipolytica* W29 strain is cultured on a dish of solid YPD for 1 day at 28° C.

Starting with an isolated colony, a liquid YPD culture (5 ml) is incubated for 40 to 48 hours at 28° C. while stirring (170 rpm).

The cells from 3 ml of culture are collected by centrifuging at 13000 rpm for 5 min.

The pellet is then suspended in 500 µl of Sorbitol Buffer (1 M Sorbitol, 0.1 M Tris-HCl; pH 8; EDTA 0.1 M).

After adding 50 µl of 3 mg/ml zymolase solution (Zymolase 100T, Seikagaku Corp. Coger) and 50 µl of β-mercaptoethanol (0.28 M), the cells are incubated at 37° C. for 1 hr.

The cells are then collected by centrifugation and placed back in suspension in 500 µl of TE (50 mM Tris-HCl; pH 8.0; 20 mM EDTA).

After adding 50 µl of 10% SDS, they are incubated for 20 min. at 65° C. Next, 200 µl of 5 M potassium acetate solution are added.

The cells are kept in ice for 30 min., prior to centrifugation (5 min., 13000 rpm).

The pellet is resuspended in 700 µl of isopropanol, centrifuged for 5 min. at 13000 rpm, and washed with 500 µl of 70% ethanol.

After the supernatant is eliminated, 400 µl of TE-Rnase A (TE+100 µg/ml of RNase A) are added and the cells are incubated for 15 min. to 1 hr. at 37° C.

The DNA is precipitated using 40 µl of potassium acetate (2.5 M; pH 5.2) and 1 ml of 100% ethanol. It is centrifuged for 5 min. at 13000 rpm and the supernatant is eliminated.

A washing with 700 µl of 70% ethanol is performed. After the pellet is dried, the genomic DNA is recovered in 100 µl of water.

Synthesizing the DNA from the GUT2 Gene

DNA synthesis from the GUT2 gene is performed using PCR (Eppendorf 2720 thermal cycler) inside a 0.5-ml microtube.

The reaction mixture is composed of 10 ng of genomic DNA from the *Yarrowia lipolytica* W29 wild type strain obtained in Example 1 in the presence of 50 pmols of each corresponding primer in the upstream (P1) and downstream (T2) regions, respectively, of the GUT2 gene's ORF, 200 µM of each dNTP, 1.5 mM $MgCl_2$, 2.5 U of Pfu (STRATAGENE, La Jolla, Calif.) and the buffer provided with the enzyme at the indicated concentration in a final volume of 50 µl.

The PCR progresses over 30 successive amplification cycles.

Each cycle is composed of a DNA denaturation step for 1 min. at 94° C., a step for hybridizing the 2 specific primers for 30 secs. at 57° C., and a DNA copy elongation step at 72° C.

The DNA fragments are recovered from agarose gels by using the QIAquick Gel Extraction Kit (Qiagen, Hilden, Germany).

Synthesizing the P and T Fragments of the GUT2 Gene and Creating the P-T Fragment The P-T (Promoter-Terminator) cassette is obtained via two PCR amplification steps.

The promoter and terminator are located, respectively, upstream and downstream of the GUT2 gene's ORF.

These two regions, approximately 1 kb long, are amplified from the genomic DNA of the *Yarrowia lipolytica* W29 wild type strain with, respectively, the P1/P2 and T1/T2 primer pairs.

The P2 and T1 primers contain the I-SceI meganuclease rare recognition site.

The obtained PCR fragments, P-I-SceI and I-SceI-T, are then reunited by ligation and used as a matrix for PCR amplification of the P-I-SceI-T (PT) cassette using the P1, T2 primers.

This cassette is then cloned into the pCR4-Blunt TOPO plasmid (INVITROGEN).

Following transformation in *E. coli*, the pCR4-TOPO-PT vector referred to as GUT2-PT (JME743) is isolated.

Obtaining the URA3 Gene:

The I-SceI URA3 cassette is obtained by I-SceI's digestion of the KS-URA3 plasmid (JME507; Fickers et al. 2003 Op. cit.).

The I-SceI-URA3 fragment is purified on agarose gel.

Insertion into the P-T fragment:

The plasmid carrying the GUT2-PT cassette (JME743) is digested by I-SceI.

Following dephosphorylation of the PT plasmid's digestion product, a ligature between this plasmid and the I-SceI-URA3 selection marker is made.

The resulting plasmids have the P-URA3-T module and are referred to as JME744 (GUT2-PUT).

The PUT disruption cassette is generated via PCR amplification using the GUT2-PUT plasmid and the P1/T2 primers.

The PCR fragment is then used to invalidate the GUT2 gene via transformation of *Y. lipolytica*.

Yeast Strain Transformation:

The method used to transform *Y. lipolytica* is based on using lithium acetate to permeabilize the cells (Gaillardin et al., 1985).

The cells (Po1d strain) are grown at 28° C. in 20 mL of YPD medium complemented by 50 mM citrate buffer, pH 4.

When the culture has a cell concentration approaching $10^8$ cells/ml, it is centrifuged.

Competence is acquired following incubation of the cells, which are resuspended in 20 ml of 0.1 M lithium acetate, pH 6, for 1 hour at 28° C. while stirring (100 rpm).

Next, the cells are centrifuged for 2 min. at 2000 rpm and are taken up in the same solution in order to obtain a concentration of $5.10^8$ cells/ml.

The transformation is performed by adding 5 µl of carrier DNA (fish) and 10 µl of transformer DNA (GUT2-PUT cassette) to 100 mL of competent cells.

The mixture is incubated without stirring at 28° C., then 0.7 ml of PEG 4000 (40%) in lithium acetate (0.1M; pH 6) is added.

This mixture is incubated while stirring (250 rpm) for one hour at 28° C. Then the cells undergo thermal shock for 1 min. at 39° C.

The mixture is diluted by adding 1.2 ml of 0.1 M, pH 6 lithium acetate solution.

Selecting and Purifying Mutant Yeast Strains Expressing the URA3 Gene.

200 µL of the transformation are spread onto each dish of YNB—casamino acids medium (uracil-free medium).

The transformants appear at between 3 and 5 days of incubation at 28° C.

A second smear starting with an isolated colony is performed in the selective medium in order to purify the transformants.

Verifying Disruption of the GUT2 Gene

Verification of the gene's deletion is performed via PCR using the specific ver11 and ver2 primers of the GUT2 gene located outside the disruption cassette.

The size of the amplified fragment enables verification of the GUT2 gene's disruption [as] compared to the size of the amplified fragment in the wild type strain with the same primers.

Excision of the URA3 Gene

The URA3ex marker used can be excised via Cre recombinase expression.

The yeast cells are transformed by the pRRQ2 plasmid (hp4d-cre, yILEU2) and the Leu+ transformants are selected on a leucine-free medium.

Next, to enable the loss of the Cre recombinase expression vector, the Leu+ transformants are grown in YPD medium for 12 hrs. starting from a YPD preculture diluted to 1/1000.

The cells are then spread onto YNB medium.

The Ura– (marker excision) and Leu– (loss of pQRR2 plasmid) clones are selected.

Excision of the marker is confirmed via PCR with the ver1/ver2 primers.

TABLE 3

| | | Transformation Operations | |
|---|---|---|---|
| Step | Mutant to Transform | Transformation Cassette | Transformed Mutant |
| 1 | Po1d, Leu–, Ura–, | PUTgut2 cassette, Ura+ selection | JMY1202, Leu–, Ura+, Δgut2 |
| 2 | JMY1202, Leu–, Ura+, Δgut2 | Genomic fragment containing the LEU2 gene | JMY1387, Leu+, Ura+, Δgut2 |

Leu+/Leu–: strain expressing/not expressing the LEU2 gene.
Ura+/Ura–: strain expressing/not expressing the URA3 gene.

Example 23

Obtaining Mutant *Yarrowia lipolytica* Yeast Strains MTLY40, MTLY64, MTLY66, MTLY82, MTLY92, MTLY95a, and JMY 1393

By using the protocol from Example 1 and following the specifications provided in Table 4 below, the mutant *Yarrowia lipolytica* yeast strains MTLY40, MTLY64, MTLY66, MTLY82, MTLY92, MTLY95a, and JMY 1393 are constructed.

The strain MTLY37 (Leu+, Ura+, Δpox2-5), previously described in international patent application WO 2006/064131, is a phototrophic strain for leucine and uracil.

TABLE 4

| | | Transformation Operations | |
|---|---|---|---|
| Step | Mutant to Transform | Transformation Cassette | Transformed Mutant |
| 1 | MTLY37, Leu+, Ura+, Δpox5-PT, Δpox2-PT, Δpox3-PT, Δpox4-PUT | Ura3-41 PCR fragment, 5FOA selection | MTLY40, Leu+, Ura–, Δpox5-PT, Δpox2-PT, Δpox3-PT, Δpox4-Pura3-41T |
| 2 | MTLY40, Leu+, Ura–, Δpox5-PT, Δpox2-PT, Δpox3-PT, Δpox4-Pura3-41T | PHTleu2 cassette, hygromycin selection | MTLY64, Leu–, Ura–, Hyg+, Δpox5-PT, Δpox2-PT, Δpox3-PT, Δpox4-Pura3-41T, leu2-PHT |
| 3 | MTLY64, Leu–, Ura–, Hyg+, Δpox5-PT, Δpox2-PT, Δpox3-PT, Δpox4-Pura3-41T, leu2-PHT | pRRQ2 vector, Leu+ selection, Hyg– verification, loss of pRRQ2 plasmid on YPD, isolation of Leu– | MTLY66, Leu–, Ura–, Δpox5-PT, Δpox2-PT, Δpox3-PT, Δpox4-Pura3-41T, Δleu2 |
| 4 | MTLY66, Leu–, Ura–, Δpox5-PT, Δpox2-PT, Δpox3-PT, Δpox4-Pura3-41T, Δleu2 | PHTpoxl cassette, hygromycin selection | MTLY82, Leu–, Ura–, Hyg+, Δpox5-PT, Δpox2-PT, Δpox3-PT, Δpox4-Pura3-41T, Δleu2, pox1-PHT |
| 5 | MTLY82, Leu–, Ura–, Hyg+, Δpox5-PT, Δpox2-PT, Δpox3-PT, Δpox4-Pura3-41T, Δleu2, pox1-PHT | pRRQ2 vector, Hyg– verification, loss of pRRQ2 plasmid on YPD | MTLY85, Leu–, Ura–, Δpox5-PT, Δpox2-PT, Δpox3-PT, Δpox4-Pura3-41T, Δleu2, Δpoxl |
| 6 | MTLY85, Leu–, Ura–, Δpox5-PT, Δpox2-PT, Δpox3-PT, Δpox4-Pura3-41T, Δleu2, Δpox1 | PHTpox6 cassette, hygromycin selection | MTLY92, Leu–, Ura–, Hyg+, Δpox5-PT, Δpox2-PT, Δpox3-PT, Δpox4-Pura3-41T, Δleu2, Δpox1, pox6-PHT |
| 7 | MTLY92, Leu–, Ura–, Hyg+, Δpox5-PT, Δpox2-PT, Δpox3-PT, Δpox4-Pura3-41T, Δleu2, Δpox1, pox6-PHT | pRRQ2 vector, Hyg– verification, loss of pRRQ2 plasmid on YPD | MTLY95a, Leu–, Ura–, Δpox5-PT, Δpox2-PT, Δpox3-PT, Δpox4-Pura3-41T, Δleu2, Δpox1, Δpox6 |
| 8 | MTLY95a, Leu–, Ura–, Δpox5-PT, Δpox2-PT, Δpox3-PT, Δpox4-Pura3-41T, Δleu2, Δpox1, ΔpoxG | PUTgut2 cassette, uracil selection | JMY1351, Leu–, Ura+, Δpox5-PT, Δpox2-PT, Δpox3-PT, Δpox4-Pura3-41T, Δleu2, Δpox1, Δpox6, Δgut2-PUT |

TABLE 4-continued

| | | Transformation Operations | |
|---|---|---|---|
| Step | Mutant to Transform | Transformation Cassette | Transformed Mutant |
| 9 | JMY1351, Leu−, Ura+, Δpox5-PT, Δpox2-PT, Δpox3-PT, Δpox4-Pura3-41T, Δleu2, Δpox1, Δpox6, Δgut2-PUT | Genomic fragment containing the LEU2 gene | JMY1393, Leu+, Ura+, Δpox5-PT, Δpox2-PT, Δpox3-PT, Δpox4-Pura3-41T, Δpox1, Δpox6, Δgut2-PUT |

Leu+/Leu−: strain expressing/not expressing the LEU2 gene.
Ura+/Ura−: strain expressing/not expressing the URA3 gene.
Hyg+/Hyg−: strain expressing/not expressing the HYG gene (hygromycin resistance).

Δpox1-PT: strain not expressing the POXn gene, by disruption using the PT fragment of gene n of POX.;

Δpox4-PUT: strain not expressing the POX4 gene, by disruption using the PUT fragment containing the URA3 gene.

Ura3-41 PCR fragment: (Mauersberger, S. et al. J. Bacteriol. 183: 5102-5109). PCR amplification of a 4650 bp fragment encompassing the URA3 gene deleted from 10 base pairs (ura3-41 allele) was performed on the genomic DNA of Y. lipolytica, JMY322 using the primers SEQ ID No. 24
Ura3-dis1 (5'GGGGTGACACTGCACTATTGGTTTG-3')
and SEQ ID No. 25
Ura3-dis2 (5'GCGTTACTGAGAGGCAGAGTACATG-3').

The PCR reaction medium is composed of 0.5 μl DNA, 1 μl of ura3-dis1 and ura3-dis2 primer, 100 pM, 4 μl. 1 of 2.5 mM dNTP, 1 unit of DNA polymerase (Ex taq, Takara), 5 μl of buffer (10× taq buffer, Takara), and 39 μl of water. The temperature setting is 94° C., 2 min., then 30 cycles of 30 sec. at 94° C., 45 sec. at 55° C., 5 min. at 72° C.

5FOA selection: Selection on a medium containing 5-FOA (5-fluoroorotic acid) enables selection of Ura− strains.

Δpox4-Pura3-41T: strain not expressing the POX4 gene, by disruption using the PUT fragment containing the URA3 marker that was converted into a ura3-41 allele by transformation with the ura3-41 fragment of the URA3 gene and that confers the Ura−phenotype.

PHTleu2 cassette: disruption cassette including a hygromycin (H) resistance gene inserted between the P and T fragments of the LEU2 gene.

Leu2/Δleu2-PHT: strain not expressing the LEU2 gene, by disruption using the PHT fragment containing the hygromycin (Hyg) resistance gene.

Hyg: Hyg (H) selection marker enabling hygromycin resistance pRRQ2 vector: replicative vector enabling cre recombinase expression and containing the LEU2 selection marker (Fickers, op. cit.).

PHTpox1 cassette: disruption cassette including a hygromycin (H) resistance gene inserted between the P and T fragments of the POX1 gene.

PHTpox6 cassette: disruption cassette including a hygromycin (H) resistance gene inserted between the P and T fragments of the POX6 gene.

YPD: YPD rich medium for losing the replicative plasmid.

Δgut2-PUT: strain not expressing the GUT2 gene of interest and expressing the URA3 selection marker inserted into a cassette between the P and T fragments.

In the following examples, the influence of the GUT2 gene's deletion under various culturing and medium composition conditions on the yeast's lipid accumulation (lipid accumulation level, accumulation rate, and type of lipid accumulated) was determined.

We found that a strain containing the Δgut2 deletion accumulates lipids more quickly and that the lipid level is higher than for a strain not containing this deletion.

Example 3

Comparison of Lipid Accumulation by a GUT2 Wild Type Strain and the Δgut2 Mutant (JMY1202) of Example 1 on Glucose A preculture of the Δgut2 mutant from Example 1, preserved on a gelose medium of the following composition: 10 g·l$^{-1}$ yeast extract, 10 g·l$^{-1}$ peptone, 10 g·l$^{-1}$ glucose, and 20 g·l$^{-1}$ Agar, is created through seeding that provides an initial absorbance at 600 nm of the preculture medium approaching 0.50.

The preculture undergoes orbital stirring (200 revs.min$^{-1}$) for 6 hrs. at 28° C. in a 50-ml ribbed vial containing 5 ml of medium composed of 10 g·l$^{-1}$ yeast extract, 10 g·l$^{-1}$ peptone, and 10 g·l$^{-1}$ glucose.

The medium used for the culture is composed of deionized water, 10 g·l$^{-1}$ yeast extract; 1.7% g·l$^{-1}$ to 20 g·l$^{-1}$ YNB; 5 ml g·l$^{-1}$ NH$_4$Cl, and 20 g·l$^{-1}$ glucose. The culture's pH is maintained by adding phosphate buffer, pH 6.8, to reach a final concentration of 50 mM.

Seeding of the culture is performed with the equivalent of an initial absorbance at 600 nm of 0.5 provided by the preculture medium.

The culture is brought up to 28° C. in 500-ml ribbed vials with 50 ml of medium at a stirring speed of 200 revs.min$^{-1}$.

At 11, 24, and 48 hours of culturing, biomass samples corresponding to 10 OD at 600 nm were taken. The supernatant is eliminated by centrifugation. 2 washings of the cell biomass are performed using 9 g·l$^{-1}$ NaCl. Next, the biomass is lyophilized and the fatty acids are extracted using the method of Folch et al. (J. Biol. Chem., 1957. 226(1): pp. 497-509).

The composition of accumulated fatty acids is determined by gas-phase chromatography on a Varian Factor Four vf-23 ms column, equipped with a flame ionization detector, following transmethylation of the fatty acids using the BF$_3$-in-methanol method described by Athenstaedt et al. (J. Bacteriol. 1999. 181(20): pp. 6441-8).

A direct transmethylation without prior extraction of the lipids according to the method described by Browse et al. (Anal. Biochem., 1986. 152(1): pp. 141-5) was also performed.

The temperature variation of the chromatograph's oven is set at 150° C. to 260° C. at the rate of 8° C. per minute.

The results show a maximum lipid production of 236 mg·l$^{-1}$ after 24 hrs.

After 11 hrs. of culturing, the lipids represent 7% of the mass for the gut2 wild type strain and 8.7% for the Δgut2 mutant, in other words, a 20% increase in the lipid content.

After 24 hrs. of culturing, part of the lipids is consumed; the lipids represent 5.7% of the mass for the wild type gut2 strain and 6.9% for the Δgut2 mutant, or a 20% increase in the lipid content.

The 16:1 (n-9), (Z)-7-hexadecenoic acid degradation intermediary represents, after 11 hours of culturing, 1.2% of the total lipids for the gut2 wild type strain and 3.01% for the Δgut2 mutant, or a 250% increase in the content of this fatty acid.

The 16:1 (n-9), (Z)-7-hexadecenoic acid degradation intermediary represents, after 24 hours of culturing, 1.68% of the total lipids for the gut2 wild type strain and 4.09% for the Δgut2 mutant, or a 240% increase in the content of this fatty acid.

Example 4

Comparison of Lipid Accumulation by the GUT2 Wild Type Strain and the Δgut2 Mutant (JMY1202) from Example 1 Starting with 65% Oleic Acid Oil The conditions from Example 3 are reproduced while replacing the glucose with oleic acid (65% purity, Sigma) in the culture medium at a concentration of 3%.

The cell biomass is washed 3 times with BSA (Bovine Serum Albumin) and once with NaCl before extracting the lipids.

After culturing for 24 hrs. 1.08 g·l$^1$ of lipids is obtained, or a production increase of approximately 450% over Example 1.

After culturing for 11 hrs., the lipids represent 14.1% of the mass for the GUT2 wild type strain and 37% for the Δgut2 mutant, or a 260% increase in the lipid content.

After culturing for 24 hrs., part of the lipids is consumed; the lipids represent 12.8% of the mass for the GUT2 wild type strain and 31.6% for the Δgut2 mutant, or a 250% increase in the lipid content.

After culturing for 11 hours, the 16:1 (n-9), (Z)-7-hexadecenoic acid degradation intermediary represents 1.14% of the total lipids for the GUT2 wild type strain and 10.4% for the Δgut2 mutant, or a 912% increase in the content of this fatty acid.

After culturing for 24 hours, the 16:1 (n-9), (Z)-7-hexadecenoic acid degradation intermediary represents 1.7% of the total lipids for the GUT2 wild type strain and 14.9% for the Δgut2 mutant, or a 880% increase in the content of this fatty acid.

After culturing for 48 hours, the 16:1 (n-9), (Z)-7-hexadecenoic acid degradation intermediary represents 1.62% of the total lipids for the GUT2 wild type strain and 25.0% for the Δgut2 mutant, or a 1560% increase in the content of this fatty acid.

Example 5

Comparison of Lipid Accumulation by the GUT2 Wild Type Strain and the Δgut2 Mutant (JMY1202) from Example 1 Starting with (99% Oleic Acid) Oil The conditions from Example 4 are reproduced while replacing the oleic oil with ultrapure (>99%) oleic acid in the culture medium at the same concentration of 3%. Under these conditions 3.45 g·l$^{-1}$ of lipids are produced in the culture medium after culturing for 11 hrs.; the quantity decreases to 2.6 g·l$^{-1}$ after 24 hrs. due to high consumption of lipid reserves.

After culturing for 11 hrs., the lipids represent 50.0% of the mass for the gut2 wild type strain and 70.1% for the Δgut2 mutant, or a 140% increase in the lipid content.

After culturing for 24 hrs., part of the lipids is consumed; the lipids represent 31.5% of the mass for the GUT2 wild type strain and 51.5% for the Δgut2 mutant, or a 160% increase in the lipid content.

After culturing for 11 hours, the 16:1 (n-9), (Z)-7-hexadecenoic acid degradation intermediary represents 3.14% of the total lipids for the GUT2 wild type strain and 12.0% for the Δgut2 mutant, or a 382% increase in the content of this fatty acid.

After 24 hours of culturing, the 16:1 (n-9), (Z)-7-hexadecenoic acid degradation intermediary represents 3.25% of the total lipids for the GUT2 wild type strain and 18.25% for the Δgut2 mutant, or a 560% increase in the content of this fatty acid.

In the following examples, the influence of culturing conditions and of the medium composition on the productivity and accumulation of unsaturated fatty acids with the Δgut2Δpox1-6 mutant was studied.

Example 6

Comparison of Lipid Accumulation by the Δgut2 Mutant (JMY1202) from Example 1 and the Δgut2Δpox1-6 Mutant (JMY 1393) from Example 2 Starting with Glucose Example 3 is repeated with the (JMY 1393) strain.

The results show a maximum lipid production of 420 mg.l$^{-1}$ after 24 hours.

The increase in lipid production as compared to the Δgut2 strain (Example 3) is due to β-oxidation blocking and the absence of lipid reserve consumption.

The total lipids represent 12.9% of the dry weight (w/w).

Example 7

Comparison of Lipid Accumulation by the Δgut2 Mutant (JMY1202) from Example 1 and the Δgut2Δpox1-6 Mutant (JMY 1393) from Example 2 Starting with Oleic Acid Example 4 is repeated with the (JMY 1393) strain in the presence of oleic acid (3%) to which glucose (0.5%) is added.

The results show a lipid production of 1.56 g·l$^{-1}$ after culturing for 11 hrs. and of 1.77 g·l$^{-1}$ after culturing for 24 hrs.

The lipids represent, at 11 hrs., 38.51% of the dry weight and 42% of the dry weight at 24 hrs.

Example 8

Separation of Lipids Accumulated on Oleic Medium into Free Fatty Acids and Triacylglycerols Starting with the culture medium at 24 hrs. from examples 4 and 7, an extraction of the total lipids is performed using the Folch method.

The purified lipids were then separated into free fatty acids (FFA) and triacylglycerols (TAG) by solid-phase extraction using an SPE Aminopropyl column (IST-France) as per the protocol of Laffargue et al. (Plant Physiol. Biochem., 2007. 45(3-4): pp. 250-257).

The composition of each lipid fraction is determined by gas-phase chromatography and is summarized in Table 5 below (the results are expressed in % of total lipids).

TABLE 5

| Mutant | Δgut2 | | Δgut2Δpox1-6 | |
|---|---|---|---|---|
| Lipids | TAG | FFA | TAG | FFA |
| C16:0 | 5.15 | 14.00 | 4.45 | 6.56 |
| C16:1 (n-9) | 14.76 | 3.95 | 0.25 | 0.06 |
| C16:1 (n-7) | 0.19 | 0.00 | 0.12 | 0.09 |
| C18:0 | 1.10 | 9.77 | 0.72 | 1.94 |
| C18:1 (n-9) | 50.16 | 58.64 | 63.58 | 70.31 |
| C18:2 (n-6) | 22.54 | 9.60 | 24.93 | 17.26 |
| Totals: | 94.11 | 96.96 | 94.04 | 96.22 |

Example 9

Comparison of Lipid Accumulation by a GUT2 Wild Type Strain and the Δgut2 (JMY1202) and Δgut2Δpox1-6 (JMY1393) Mutant Strains from Examples 1 and 2 Starting with a Medium Containing Oleic Acid and Glucose The process from Example 3 is repeated with a culture medium composed of deionized water, 10 g·l$^{-1}$ yeast extract, 20 g·l$^{-1}$ proteose peptone, 5 ml·l$^{-1}$ NH$_4$Cl, 40 g·l$^{-1}$ glucose, and 30 g·l$^{-1}$ oleic acid (65% purity, Sigma). The culture's pH is maintained by adding phosphate buffer at 6.8 pH up to a final concentration of 50 mM.

Under these conditions the quantity of accumulated lipids is as follows:

| | 24 hrs. | 48 hrs. | 72 hrs. |
|---|---|---|---|
| Δgut2 | 2.55 g·l$^{-1}$ | 6.71 g·l$^{-1}$ | 8.24 g·l$^{-1}$ |
| Δgut2Δpox1-6 | 4.12 g·l$^{-1}$ | 7.27 g·l$^{-1}$ | 9.1 g·l$^{-1}$ | the dry weight percentage in lipids is as follows:

| | 11 hrs. | 24 hrs. | 48 hrs. | 72 hrs. |
|---|---|---|---|---|
| gut2 | 7.2% | 10.6% | — | — |
| Δgut2 | 12.0% | 18.0% | 23.0% | 20.0% |
| Δgut2Δpox1-6 | 25.0% | 29.0% | 35.0% | 35.0% |

All of the obtained results show the advantage of using mutant yeast strains of the invention for lipid production.

Example 10

Comparative Analysis of Lipid Production by the Wild Type Strains (W29), delta gut2 (derived from JMY1202 rendered prototrophic, JMY1387) and delta gut2 delta Pox1-6 (JMY1393)

The reactor cultures are made in fed-batch mode in a fermenter (Braun Biostate E) with a capacity of 20 effective liters.

The various available functions are:
Measurement and regulation of temperature, pH, dissolved oxygen, pressure,
Foam detection with regulated addition of antifoaming agent,
Control of live-steam sterilization procedure,
Feed pump control,
Balance weight reading.

The pH is regulated by two peristaltic pumps, one drawing in a basic solution (10 mol·l$^{-1}$ potassium or ammonia hydroxide), the other drawing in an acid solution (0.29 mol·l$^{-1}$ orthophosphoric acid). A third peristaltic pump allows an antifoaming agent (Strucktol) to be added in regulated amounts.

The bioreactor is fed with a carbonate substrate (glucose solution: 700 to 750 g/l) by controlling two volumetric pumps (high and low airflow). A third pump, which draws in the substrate, allows a concentrated saline solution to be added at a rate 10 times lower than that of the substrate.

TABLE 6

Composition of the Saline Feeding Solution for *Y. lipolytica*

| Compound | Concentration [g · l$^{-1}$] |
|---|---|
| KCl | 20.000 |
| NaCl | 20.000 |
| MgSO$_4$•; 7H$_2$O | 27.000 |
| ZnSO$_4$•; 7H$_2$O | 7.710 |
| MnSO$_4$•; H$_2$O | 0.470 |
| CoCl$_2$•; 6H$_2$O | 0.300 |
| CuSO$_4$•; 5H$_2$O | 0.600 |
| Na$_2$MoSO$_4$•; 2H$_2$O | 0.094 |
| CaCl$_2$•; 2H$_2$O | 6.400 |
| FeSO$_4$•; 7H$_2$O | 3.970 |
| H$_3$BO$_3$ | 0.300 |
| H$_3$PO$_4$ | 125.000 |

The combined supply of the saline medium and of the carbonate substrate ensures that the nutritional needs of the biomass (growth phase) are met, except for nitrogen. A final pump supplies nitrogen in controlled fashion in very small amounts during the low-nitrogen lipid accumulation phase.

The entering gas mass flow (supplied oxygen) is measured and regulated, as is the stirring speed (Rhuston turbine).

The starter that seeds the reactor culture is obtained after a series of three precultures:
1. preculture I of 8 ml YPD for 24 hrs. at 30° C. inside a 100-ml vial.
2. preculture II of 72 ml of minimal medium is seeded with culture I, incubated for 12 hrs. at 30° C. inside a 250-ml vial.
3. preculture III of 720 ml of minimal media is seeded with culture II, incubated for 12 hrs. at 30° C. inside a 5000-ml vial. The bioreactor is then seeded with the latter preculture.

0.8 g of glucose and 1% of vitamin solution concentrate are added to the minimal medium. The composition of the minimal medium and of the concentrated vitamin solution is described in Table 7 and Table 8.

TABLE 7

Composition of the Minimal Medium

| Compound | Concentration [g · l$^{-1}$] |
|---|---|
| MgSO$_4$•; 7H$_2$O | 5.278 |
| CaCl$_2$•; 2H$_2$O | 0.051 |
| FeSO$_4$•; 7H$_2$O | 0.215 |

TABLE 7-continued

Composition of the Minimal Medium

| Compound | Concentration [g · l$^{-1}$] |
|---|---|
| ZnSO$_4$•; 7H$_2$O | 0.078 |
| CuSO$_4$•; 5H$_2$O | 0.009 |
| CoCl$_2$•; 6H$_2$O | 0.158 |
| MnSO$_4$•; H$_2$O | 0.009 |
| Na$_2$MoSO$_4$•; 2H$_2$O | 0.0360 |
| H$_3$PO$_4$ | 28.620 |
| H$_2$SO$_4$ | 16.370 |
| H$_3$BO$_3$ | 0.0025 |
| KCl | 7.450 |

TABLE 8

Composition of 1000X Vitamin Solution Concentrate

| Compound | Concentration [g · l$^{-1}$] |
|---|---|
| d-biotin | 0.05 |
| Panthotenate | 1.00 |
| Nicotinic acid | 1.00 |
| Thiamine hydrochloride | 1.00 |
| p-amino-benzoic acid | 0.20 |
| Pyridoxol hydrochloride | 1.00 |
| Myoinositol | 25.00 |

Samples are taken at regular intervals inside the reactor; on these samples, measurements are taken of:
the quantity of solids corresponding to the total biomass, using the gravimetric method after filtering a specific volume of yeast suspension.
the quantity of lipids. The total lipid quantity is determined using a method derived from Folch's method: Folch, J. Lees, M., Slane-Stanley, J. (1957), A Simple Method for the Isolation and Purification of Total Lipids from Animal Tissues. J Biol Chem 226: 497-509.

Three cell cultures were created in a fully-controlled environment that carefully controlled, in particular, the growth rate and lipid accumulation kinetics by meticulously monitoring nitrogen limitation. The first cell culture of the *Y. lipolytica* W29 wild type strain is used as a reference culture in order to compare the performance of the two Δgut2 and Δgut2Δpox1-6 mutant strains.

The cell cultures pass through various phases, namely:
Phase 1 (t<13-15 hrs.): exponential-phase cell growth (growth rate controlled by carbonate substrate supply).
Phase 2 (13-15 hrs.<t<16-21 hrs.): start of nitrogen limitation (change in pH regulation from ammonia to potassium hydroxide), start of lipid accumulation (excess carbonate substrate supply) and slowing of cell growth (growth rate controlled by external nitrogen supply).
Phase 3 (t>21 hrs.): accumulation The results from the W29 wild type strain reactor culture (FIG. 6) show a maximum cell concentration of 60 g·l$^{-1}$ and a maximum lipid content of 0.42 $g_{lip}g_x^{-1}$ after 78 hrs of reactor culturing. During this culture, the lipid accumulation phase was initiated at 16 hrs. There is no intracellular lipid consumption phase.

The results from the Δgut2 mutant strain reactor culture (FIG. 7) show a maximum cell concentration of 103 g·l$^{-1}$, or an increase of over 70% in comparison with the wild type strain, and a maximum lipid content of 0.47 $g_{lip}g_x^{-1}$ after 47 hrs., or an increase of 13% of reactor culture over a time period that was 40% shorter. During this culture, the lipid accumulation phase was initiated at 18 hrs. There is no intracellular lipid consumption phase but the lipid content reached a horizontal asymptote tending towards 0.47 $g_{lip}g_x^{-1}$.

The results from the Δgut2Δpox1-6 mutant strain reactor culture (FIG. 8) show a maximum cell concentration of 102 g·l$^1$, or an increase of over 70% in comparison with the wild type strain, and a maximum lipid content of 0.47 $g_{lip}g_x^{-1}$ after 84 hrs., or an increase of 13% of reactor culture over a time period that was 40% shorter. During this culture, the lipid accumulation phase was initiated at 21 hrs. There is no intracellular lipid consumption phase but the culture was stopped when the lipid content began to stagnate.

Assessment (FIG. 9)
By tracking yields and instant productivity rates, it is possible to compare the strains by using the best performances obtained for each culture.

Of note: the Δgut2 strain has a total glucose-into-lipids conversion yield that is 10% higher than the wild type strain, and a volumetric productivity ([$g_{lip}g_x^{-1}$]) of over 19%. As regards the Δgut2Δpox1-6 strain, the improvement in performance over the wild type strain is 24% for the yield and 20% for productivity.

The invention claimed is:

1. A mutant yeast strain of *Yarrowia lipolytica* not expressing the glycerol-3-phosphate dehydrogenase (GUT2) gene and which is able to accumulate lipids, which in addition does not express at least one gene responsible for β-oxidation of lipids selected from the acyl-coenzyme A oxidase (POX) genes (POX1 through POX6), the multifunctional beta-oxidation protein (MFE1) gene or the peroxisomal oxoacyl thiolase (POT1) gene.

2. The mutant yeast strain of *Yarrowia lipolytica* not expressing the glycerol-3-phosphate dehydrogenase (GUT2) gene, wherein said strain is the JMY1202, |delta|gut2 strain deposited with the National Collection of Microorganism Cultures (CNCM, Pasteur Institute, 25, rue du Docteur Roux, F-75724 Paris Cedex 15) as CNCM No. 1-4038, on Jul. 8, 2008.

3. The mutant yeast strain of claim 1 which in addition does not express the POX2 through POX5 genes.

4. The mutant yeast strain of claim 1 which in addition does not express the POX1 through POX6 genes.

5. The mutant yeast strain of claim 4, wherein said strain is the JMY1393, |delta|gut2|delta|pox1-6 strain deposited with the National Collection of Micro-organism Cultures (CNCM, Pasteur Institute, 25, rue du Docteur Roux, F-75724 Paris Cedex 15) as CNCM No. 1-4169, on May 28, 2009.

6. A method for obtaining a mutant *Yarrowia lipolytica* yeast strain of claim 1 that does not express the GUT2 gene, which does not carry out β-oxidation of lipids comprising the steps:
   a. constructing a disruption cassette that includes the promoter (P) and terminator (T) sequences of the GUT2 yeast gene flanking a selection marker gene wherein said selection marker gene is flanked on either side of its coding sequence by one or more cross-over sequence(s);
   b. introducing said disruption cassette into a yeast strain which does not express at least one gene responsible for β-oxidation of lipids selected from the acyl-coenzyme A oxidase (POX) genes (POX1 through POX6), the multifunctional beta-oxidation protein (MFE1) gene or the peroxisomal oxoacyl thiolase (POT1) gene: and
   c. selecting, from among the yeast strains transformed by introduction of said disruption cassette, a yeast strain that is defective for the GUT2 gene;
   to thereby obtain a mutant yeast strain that does not express the GUT2 gene and which does not carry out β-oxidation of lipids.

7. The method of claim 6 wherein said strain selected in step c) is transformed with a vector enabling the expression of a recombinase thereby obtaining a yeast strain that does not express the GUT2 gene and no longer expresses the marker gene.

8. The method of claim 6 wherein in step a) said disruption cassette is constructed according to a method comprising the steps:
   a. forming a construct in which the Promoter (P) sequences and the Terminator (T) sequences of a yeast GUT2 gene flank a restriction site to form disruption cassette 2 having the structure P/restriction site/T; and
   b. introducing, at the restriction site of disruption cassette 2, a gene encoding a selection marker, to form disruption cassette 1 having the structure P/restriction site/marker/restriction site/T where in disruption cassette 1 is the disruption cassette formed in step a.

9. The method of claim 8 wherein DNA fragments containing either the Promoter (P) sequence or the Terminator (T) sequence of the GUT2 yeast gene are synthesized using PCR.

10. The method of claim 9 wherein PCR is performed on *Yarrowia lipolytica* DNA using as primers the pairs G3P-P1/G3P-P2(SEQ ID Nos. 2 and 3) for the P sequence and G3P-T1/G3P-T2(SEQ ID Nos. 4 and 5) for the T sequence.

11. The method of claim 10 wherein the G3P-P2 and G3P-T1 primers each additionally include a restriction site sequence.

12. The method of claim 8 wherein disruption cassette 1 is introduced into a yeast strain that is a wild type yeast strain or a yeast strain that does not express the selection marker gene contained in the disruption cassette.

13. The method of claim 12 wherein the yeast strain that does not express the selection marker gene contained in the disruption cassette is a Po1d strain.

14. The method of claim 6 wherein the mutant yeast strain that does not carry out β-oxidation of lipids is a strain that does not express at least one gene responsible for lipid β-oxidation.

15. The method of claim 14 wherein said mutant yeast strain does not express at least the POX 2, POX 3, POX 4, or POX 5 genes.

16. The method of claim 14 wherein said mutant yeast strain does not express at least the POX 1, POX 2, POX 3, POX 4, POX 5, or POX 6 genes.

17. The method of claim 16 wherein the mutant yeast strain is selected from among the group consisting of MTLY37, MTLY40, MTLY64, MTLY66, MTLY82, MTLY85, MTLY92, and MTLY95a strains.

18. A method for synthesis of lipids employing a mutant yeast strain of claim 1.

19. The method of claim 18 wherein the lipids comprise free fatty acids and triacylglycerols.

20. The method of claim 18 wherein the lipids comprise n-2 fatty acids.

21. The method of claim 18 comprising the steps:
   a. growing the mutant yeast strain in an appropriate medium to produce lipids; and
   b. collecting the lipids produced.

22. The method of claim 18 wherein the mutant yeast strain is the *Yarrowia lipolytica* JMY1393 strain (CNCM 1-4169).

23. A method for synthesis of lipids employing the mutant yeast strain of claim 2.

* * * * *

UNITED STATES PATENT AND TRADEMARK OFFICE
CERTIFICATE OF CORRECTION

PATENT NO.        : 8,597,931 B2
APPLICATION NO.   : 13/003757
DATED             : December 3, 2013
INVENTOR(S)       : Nicaud et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 162 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 25

<210> SEQ ID NO 1
<211> LENGTH: 4140
<212> TYPE: DNA
<213> ORGANISM: Yarrowia lipolytica
<220> FEATURE:
<221> NAME/KEY: misc_feature
<222> LOCATION: (1)..(4140)
<223> OTHER INFORMATION: DNA containg fragment P and fragment T flanking
      the GUT2 gene
<220> FEATURE:
<221> NAME/KEY: misc_feature
<222> LOCATION: (1)..(20)
<223> OTHER INFORMATION: Primer ver 1 for verification of deletion of
      the GUT2 gene
<220> FEATURE:
<221> NAME/KEY: misc_feature
<222> LOCATION: (17)..(36)
<223> OTHER INFORMATION: Primer P1 for synthesis of fragment P1 of the
      GUT2 gene
```

```
<220> FEATURE:
<221> NAME/KEY: misc_feature
<222> LOCATION: (1114)..(1135)
<223> OTHER INFORMATION: Primer P2 for the synthesis of the GUT2 gene
<220> FEATURE:
<221> NAME/KEY: misc_feature
<222> LOCATION: (1151)..(2989)
<223> OTHER INFORMATION: sequence coding GUT2
<220> FEATURE:
<221> NAME/KEY: misc_feature
<222> LOCATION: (3067)..(3085)
<223> OTHER INFORMATION: Primer T1 for synthesis of fragment T of the
      GUT2 gene
<220> FEATURE:
<221> NAME/KEY: misc_feature
<222> LOCATION: (3863)..(3883)
<223> OTHER INFORMATION: Primer T2 for the synthesis of fragment T of
      the GUT2 gene
<220> FEATURE:
<221> NAME/KEY: misc_feature
<222> LOCATION: (4116)..(4140)
<223> OTHER INFORMATION: Primer ver 2 for verification of deletion of
      the GUT2 gene

<400> SEQUENCE: 1
gaatgacggg ggcaacgcag atccactgtc aagccgagtc tgtccgccac gcatcatgtg      60
atagaggcta gggagtcatg tgaatatgtc acacctggat gacctctaca tacaagagcg     120
gtttgttttc tatggcatgt tgttgacgca tgctgccaac ggctattcaa cggtgacaac     180
ggatgatgct gtcacatgac gccatttttt atgttgtatc aacagcacg gtactaaaac     240 aggccatttg taaaggcctc actcagctca cacacgctca acggtcacga taaggtcgca     300
ctagaggcgt tagttggttt caagaatagt ggttattggt cttgggatac gggttggaca     360
atatacaaat gggctcgcgt acacttatac agtcctacca ttctgtcgcc ctctgattct     420
ccgccacatc agccacgccg caacgtctcc tcctcatccc cctcctgctc ttccactcgc     480
aaaacgtcca aactcaattg tgtcaaaatt ggaggttctc ttcgtttgag cctaccattt     540
tcaatttttt agttgcgaca gcggcccggt cagaggttca caacaaggtc tagagacact     600
ttgtcatggg gccgagaagg accataaaaa ccaaacgatg gtcacgtcag gtcaattact     660
gaccagtctc acatccgacc cctcgcgtgc tcgaccggag gatttctctg cactcgtcct     720 tgcataccctc ggctagcggg atttattcac caatcacaca gccgagagtt tttccggacc     780
cttcatccaa cagcttagag ttgcatgagt cagtagcaac gtagactttg agcctttgtg     840
acagatgtcc aagtgcagca cgttgtagga aaataaggtg aaggattggc caatgtgaac     900
agaggcgaca agagtccgtc tggagggctt gttgtagtca attgcccgcg caattgattg     960
acctcatcgt ttctgccgga acccccccac aagcccggat aaatagacac gccccacaag    1020
ccgttcgtct ggtctgctca cagcacactt ccatttaaaa ttcaaacaaa gcgcaccacc    1080
gcaaagcata cttaacccac tcaatgtaga cgtcgcggaa cttctctttc ctacccacca    1140
ccccaaacaa atgttcagaa ccattcgaaa accgcgtgg gctgctgccg ccgccgtggc    1200
agccgctggc gctggagccg tcgccctgtc tgtgcctgcc caggcccagg aggagctcca    1260
caagaagcac aaattcacag tgcccccgt ggccgccgag ccccctctc gagccgccca    1320 gctcgagaag atgaagaccg aggagtttga tctcgtcgtt gttggtggag gagctaccgg    1380
atccggtatc gccctcgacg ctgtcacacg aggcctcaag gttgctctgg tcgagcgaga    1440
cgatttctcc tgcggaacct cgtcccgatc caccaagctc atccacggag gtgtccgata    1500
cctcgagaag gctgtgtgga acctcgacta caacccagtac gagctggtca aggaggccct    1560
gcacgagcga aaggtcttcc tcgacattgc tccccaccct accttgtct tgcccatcat    1620
```

```
gatccccgtc tacacctggt ggcagcttcc ctacttctgg atgggtgtca agtgctacga    1680
tctgcttgcc ggccgacaga acctcgagtc ctcttacatg ctctcccgat cccgtgctct    1740
cgatgccttc cccatgcttt ccgatgacaa gctcaagggc ccattgtct actatgatgg     1800 ctcccagaac gactctcgaa tgaacgtttc tcttattatg actgctgttg agaagggtgc    1860
caccatcctg aaccattgcg aggtcaccga gctcaccaag ggcgccaatg ccagctcaa     1920 cggtgttgtt gccaaggata ctgacggaaa cgctggatcc ttcaacatca aggccaagtg    1980
tgtcgttaat gctactggac ccttcactga ctctctgcga cagatggacg acaagaacac    2040
caaggagatc tgtgctcctt cctccggtgt tcacatcatt ctccccggtt actactcccc    2100
caagaagatg ggactccttg accccgctac ttctgacggc cgagttatct tcttcctccc    2160
ctggcaggga acaccccttg ccggtactac tgaccagcct accaagatca ctgctaaccc    2220
tatcccctcc gaggaggaca ttgacttcat tctcaacgag gtccgacact acgttgaggg    2280
caaggttgat gtgcgacgag aggacgttct ggccgcctgg tccggaatcc gaccccttgt    2340
ccgggacccc cacgccaaga acaccgagtc tcttgtccga aaccatctca tcacctactc    2400
cgagtctggt cttgtcacca ttgctggcgg aaagtggacc acttaccgac agatggctga    2460
ggagactgtc gatgcctgca ttgccaagtt cggtctcaag cctgaaatct ccgccaaggc    2520
cgtcacccga gacgtcaagc tcatcggtgc taaggactgg actcctctca cttacattga    2580
tctgatccag caggaggacc ttgaccccga ggttgctaag cacctttctg agaactacgg    2640
atctcgagct ttcaccgttg cttctcttgc tgagatgccc accccgaac ccggtgtgat     2700 cccccagtct actctcacaa agggtaagcg aatcctgtac ccctacccct acctcgatgc    2760
cgagtgcaag tactctatga agtacgagta tgccaccacc gccatcgact ccttgctcg     2820 acgaactcgt cttgctttcc ttaacgccgc tgccgcctac gaggctctcc ctgaggtcat    2880
tgagatcatg gccaaggagc tccagtggga cgaggctcga aaggagcagg aattcaacac    2940
cggtgtcgag tacctctact ccatgggcct taccccaag gacaaataac tgtatagtaa     3000
aagcgtatag ccaataagat aatcacttga atgaaggagc agcaactcgt atgtttagca    3060
cttcaacgga ctatttcccc gcagcaaaga gactattgct gagttgttga gtatctgctt    3120
tacaataatg gggtatggac acacaaggag gggtcttagt gagaagttag ataggtctag    3180
catacatgag atcaatgtgg tcttacctat atcgtttgtt atcatttatc ttggtttgaa    3240
ttgataacac gagttgttca ttgaagtgat ggcaccgggt ctcacacgca acagttggcg    3300
aacaggtcgt attgttcctt agatacgacg ctcttttgga catgatggga agtgaaacta    3360
caattacagt agctacatag cttggctaac tagaccgctt acagaaccag tagtcgtcac    3420
aagaccacca cgaacaaagt ccaactaccc cactcccacc actcgtattt acttaccgca    3480
gatcacacgc ttcggtgtat ctccgtgggg catcgtgggg cattgttcta agttttccgt    3540
atggtgcaca gtcggtacgt gctttgacta accagtagaa gttaggctac tgtagtggag    3600
attgagcaat gaaacgatga caggaagacc ccaaaatgcg accacctcaa ctatacacgg    3660
cttgttgcta ttgccgcctt gcactccaca cagcaaacat gcacacgata tgcactcaag    3720
tcttaaccga atgaaggtaa aagtagcaac caacaagcga gagttactgt atacttacaa    3780
gttatacgac agtctcactt atcaccaatt ggcaacttga ccgcacagac aaacacccta    3840
caatgacctt cctcaatgtg ctctactacg tgctgctggc tgccatcatg atcggcaccg    3900
gctacttcta ctacctgtgg ttcactgaga ccaacgacca aaccgagaag atcatcagag    3960
ctgcgcttgg agtctttgat atcgccatct ggtacattct aggtatctcc acctcctttta  4020
```

```
agatcctcac ccagatgatt ctcgcctgtt tccttgtggt tctggctggt cttaagatct    4080
acatcaaccc tcgagttgga ggggctcttc tggccggcag tctgctattt gtggctgctg    4140
```

<210> SEQ ID NO 2
<211> LENGTH: 20
<212> TYPE: DNA
<213> ORGANISM: Artificial sequence
<220> FEATURE:
<223> OTHER INFORMATION: Primer for synthesis of fragment P of the GUT2
      gene

<400> SEQUENCE: 2

```
gcagatccac tgtcaagccg                                                  20
```

<210> SEQ ID NO 3
<211> LENGTH: 44
<212> TYPE: DNA
<213> ORGANISM: Artificial sequence
<220> FEATURE:
<223> OTHER INFORMATION: Primer for synthesis of fragment P of the GUT2
      gene
<220> FEATURE:
<221> NAME/KEY: misc_feature
<222> LOCATION: (1)..(22)
<223> OTHER INFORMATION: Site I-SceI in the primer G3P-P1 for synthesis
      of fragment P of the GUT2 gene

<400> SEQUENCE: 3

```
gctagggata acagggtaat gcggtaggaa agagaagttc cgcg                       44
```

<210> SEQ ID NO 4
<211> LENGTH: 41
<212> TYPE: DNA
<213> ORGANISM: Artificial sequence
<220> FEATURE:
<223> OTHER INFORMATION: Primer for synthesis of fragment T of the GUT2
      gene
<220> FEATURE:
<221> NAME/KEY: misc_feature
<222> LOCATION: (1)..(22)
<223> OTHER INFORMATION: Site I-SceI in primer G3P-T1 for synthesis of
      fragment T of theGUT2 gene

<400> SEQUENCE: 4

```
gcattaccct gttatcccta gccggactat ttccccgcag c                          41
```

<210> SEQ ID NO 5
<211> LENGTH: 21
<212> TYPE: DNA
<213> ORGANISM: Artificial sequence
<220> FEATURE:
<223> OTHER INFORMATION: Primer for synthesis of fragment T of the GUT2
      gene

<400> SEQUENCE: 5

```
gcagccagca gcacgtagta g                                                21
```

<210> SEQ ID NO 6
<211> LENGTH: 20
<212> TYPE: DNA
<213> ORGANISM: Artificial sequence
<220> FEATURE:
<223> OTHER INFORMATION: Primer for verification of deletion of the GUT2
      gene

<400> SEQUENCE: 6

```
gaatgacggg ggcaacgcag                                                  20
```

```
<210> SEQ ID NO 7
<211> LENGTH: 25
<212> TYPE: DNA
<213> ORGANISM: Artificial sequence
<220> FEATURE:
<223> OTHER INFORMATION: Primer for verification of deletion of the GUT2
      gene

<400> SEQUENCE: 7
cagcagccac aaatagcaga ctgcc                                           25

<210> SEQ ID NO 8
<211> LENGTH: 34
<212> TYPE: DNA
<213> ORGANISM: Artificial sequence
<220> FEATURE:
<223> OTHER INFORMATION: Primer for synthesis of fragment P of the LEU2
      gene
<220> FEATURE:
<221> NAME/KEY: misc_feature
<222> LOCATION: (3)..(8)
<223> OTHER INFORMATION: Site Xba in primer LEU2-P1 for synthesis of
      fragment P of the LEU2 gene

<400> SEQUENCE: 8
aatctagatg gtcacagtgg aatcatgttc gtgg                                 34

<210> SEQ ID NO 9
<211> LENGTH: 45
<212> TYPE: DNA
<213> ORGANISM: Artificial sequence
<220> FEATURE:
<223> OTHER INFORMATION: Primer for synthesis of fragment P of the LEU2
      gene
<220> FEATURE:
<221> NAME/KEY: misc_feature
<222> LOCATION: (1)..(20)
<223> OTHER INFORMATION: Site I-SceI in primer LEU2-P2 for the synthesis
      of fragment P of the LEU2 gene

<400> SEQUENCE: 9
cattaccctg ttatccctag gttccattgt ggatgtgtgt ggttg                     45

<210> SEQ ID NO 10
<211> LENGTH: 39
<212> TYPE: DNA
<213> ORGANISM: Artificial sequence
<220> FEATURE:
<223> OTHER INFORMATION: Primer for synthesis of fragment T of the LEU2
      gene
<220> FEATURE:
<221> NAME/KEY: misc_feature
<222> LOCATION: (1)..(20)
<223> OTHER INFORMATION: Site I-SceI in primer LEU2-T1 for synthesis of
      fragment T of the LEU2 gene

<400> SEQUENCE: 10
ctagggataa cagggtaatg ctctgggtct gctgccctc                            39

<210> SEQ ID NO 11
<211> LENGTH: 41
<212> TYPE: DNA
<213> ORGANISM: Artificial sequence
<220> FEATURE:
<223> OTHER INFORMATION: Primer for the synthesis of fragment Tof the
      LEU2 primer
<220> FEATURE:
<221> NAME/KEY: misc_feature
<222> LOCATION: (4)..(10)
<223> OTHER INFORMATION: Site Hind III in primer LEU2-T2 for synthesis
      of  fragment T of the LEU2 gene
```

-continued

```
<400> SEQUENCE: 11
agtaagctta gatctgttcg gaaatcaacg gatgctcaac c                              41

<210> SEQ ID NO 12
<211> LENGTH: 24
<212> TYPE: DNA
<213> ORGANISM: Artificial sequence
<220> FEATURE:
<223> OTHER INFORMATION: Primer for synthesis of fragment P of the  POX1
      gene

<400> SEQUENCE: 12
catggagtgg atcgctcgag gacg                                                 24

<210> SEQ ID NO 13
<211> LENGTH: 42
<212> TYPE: DNA
<213> ORGANISM: Artificial Sequence
<220> FEATURE:
<223> OTHER INFORMATION: Primer for synthesis of fragment P of the POX1
      gene
<220> FEATURE:
<221> NAME/KEY: misc_feature
<222> LOCATION: (1)..(22)
<223> OTHER INFORMATION: Site I-SceI in primer POX1-P2 for synthesis of
      fragment P of the POX1 gene

<400> SEQUENCE: 13
gcattaccct gttatcccta gccaggagga tcggtgaatg tg                             42

<210> SEQ ID NO 14
<211> LENGTH: 45
<212> TYPE: DNA
<213> ORGANISM: Artificial sequence
<220> FEATURE:
<223> OTHER INFORMATION: Primer for synthesis of fragment T of the POX1
      gene
<220> FEATURE:
<221> NAME/KEY: misc_feature
<222> LOCATION: (1)..(22)
<223> OTHER INFORMATION: Site I-SceI in primer POX1-T1 for synthesis of
      fragment T of the POX1 gene

<400> SEQUENCE: 14
gctagggata acagggtaat gccttgttcc gagaagagga ggacg                          45

<210> SEQ ID NO 15
<211> LENGTH: 19
<212> TYPE: DNA
<213> ORGANISM: Artificial sequence
<220> FEATURE:
<223> OTHER INFORMATION: Primer for synthesis of fragment T of the POX1
      gene

<400> SEQUENCE: 15
cggcagtggc tcaccaagc                                                       19

<210> SEQ ID NO 16
<211> LENGTH: 19
<212> TYPE: DNA
<213> ORGANISM: Artificial sequence
<220> FEATURE:
<223> OTHER INFORMATION: Primer for verification of deletion of the
      POX1 gene

<400> SEQUENCE: 16
atccagacct ccaggcggg                                                       19
```

<210> SEQ ID NO 17
<211> LENGTH: 23
<212> TYPE: DNA
<213> ORGANISM: Artificial sequence
<220> FEATURE:
<223> OTHER INFORMATION: Primer for verification of deletion of the POX1 gene

<400> SEQUENCE: 17
gctgcgtctc aatctggcga atg                                          23

<210> SEQ ID NO 18
<211> LENGTH: 28
<212> TYPE: DNA
<213> ORGANISM: Artificial sequence
<220> FEATURE:
<223> OTHER INFORMATION: Primer for synthesis of fragment P of the POX6 gene

<400> SEQUENCE: 18
ccaagctcta agatcatggg gatccaag                                     28

<210> SEQ ID NO 19
<211> LENGTH: 43
<212> TYPE: DNA
<213> ORGANISM: Artificial sequence
<220> FEATURE:
<223> OTHER INFORMATION: Primer for the synthesis of fragment P of the POX6 gene
<220> FEATURE:
<221> NAME/KEY: misc_feature
<222> LOCATION: (1)..(22)
<223> OTHER INFORMATION: Site i-SceI in primer POX6-P2 for synthesis of fragment P of thePOX6 gene

<400> SEQUENCE: 19
gcattaccct gttatcccta gcgttgaggg actgttgaga gag                    43

<210> SEQ ID NO 20
<211> LENGTH: 47
<212> TYPE: DNA
<213> ORGANISM: Artificial sequence
<220> FEATURE:
<223> OTHER INFORMATION: Primer for synthesis of fragment T of the POX6 gene
<220> FEATURE:
<221> NAME/KEY: misc_feature
<222> LOCATION: (1)..(22)
<223> OTHER INFORMATION: Site I-SceI in primer POX6-T1 for synthesis of fragment T of the POX6 gene

<400> SEQUENCE: 20
gctagggata acagggtaat gcgatgagga aatttgctct cttgagg                47

<210> SEQ ID NO 21
<211> LENGTH: 28
<212> TYPE: DNA
<213> ORGANISM: Artificial sequence
<220> FEATURE:
<223> OTHER INFORMATION: Primer for synthesis of fragment T of the POX6 gene

<400> SEQUENCE: 21
atctcgagat tggtcccctc aaacacac                                     28

<210> SEQ ID NO 22
<211> LENGTH: 21
<212> TYPE: DNA
<213> ORGANISM: Artificial sequence

```
<220> FEATURE:
<223> OTHER INFORMATION: Primer for verification of deletion of the POX6
      gene

<400> SEQUENCE: 22
gctcaagaag gtagctgagt c                                              21

<210> SEQ ID NO 23
<211> LENGTH: 23
<212> TYPE: DNA
<213> ORGANISM: Artificial sequence
<220> FEATURE:
<223> OTHER INFORMATION: Primer for verification of deletion of the POX6
      gene

<400> SEQUENCE: 23
cattaagtgt cagatcagct cgc                                            23

<210> SEQ ID NO 24
<211> LENGTH: 25
<212> TYPE: DNA
<213> ORGANISM: Artificial sequence
<220> FEATURE:
<223> OTHER INFORMATION: Primer for fragment containing ura3-41 allele

<400> SEQUENCE: 24
ggggtgacac tgcactattg gtttg                                          25

<210> SEQ ID NO 25
<211> LENGTH: 25
<212> TYPE: DNA
<213> ORGANISM: Artificial sequence
<220> FEATURE:
<223> OTHER INFORMATION: Primer for fragment containing the ura3-41
      alele

<400> SEQUENCE: 25
gcgttactga gaggcagagt acatg                                          25
```